US012611198B2

(12) United States Patent
Tanigawa

(10) Patent No.: US 12,611,198 B2
(45) Date of Patent: Apr. 28, 2026

(54) ULTRASONIC DIAGNOSTIC DEVICE, STORAGE MEDIUM, AND METHOD FOR CHANGING IMAGING CONDITIONS

(71) Applicant: GE Precision Healthcare LLC, Waukesha, WI (US)

(72) Inventor: Shunichiro Tanigawa, Hino (JP)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/675,929

(22) Filed: May 28, 2024

(65) Prior Publication Data

US 2024/0398388 A1      Dec. 5, 2024

(30) Foreign Application Priority Data

May 29, 2023     (JP) ................................. 2023-088132

(51) Int. Cl.
*A61B 8/00*          (2006.01)
(52) U.S. Cl.
CPC .............. *A61B 8/54* (2013.01); *A61B 8/5223* (2013.01)
(58) Field of Classification Search
CPC . A61B 5/7624; A61B 5/7267; G01N 29/4481
See application file for complete search history.

(56) References Cited

U.S. PATENT DOCUMENTS

| | | | | |
|---|---|---|---|---|
| 2012/0095338 A1* | 4/2012 | Mo | ........................ | A61B 8/00 600/443 |
| 2018/0140281 A1* | 5/2018 | Imai | ..................... | A61B 8/5207 |

| | | | | |
|---|---|---|---|---|
| 2018/0344289 A1* | 12/2018 | Imai | ........................ | A61B 8/467 |
| 2019/0038261 A1* | 2/2019 | Ebata | ....................... | A61B 8/469 |
| 2019/0130564 A1* | 5/2019 | Kawabata | ............. | G06T 7/0012 |
| 2019/0239857 A1* | 8/2019 | Nakajima | ............ | A61B 8/5246 |
| 2020/0375577 A1* | 12/2020 | Wohlschlager | .......... | A61B 8/54 |
| 2021/0177373 A1* | 6/2021 | Xie | ........................ | A61B 8/463 |
| 2021/0353260 A1* | 11/2021 | Srinivasa Naidu | ......................... G01S 7/52085 |

FOREIGN PATENT DOCUMENTS

| | | |
|---|---|---|
| JP | 2018153561 A | 10/2018 |
| JP | 6423540 B2 | 11/2018 |
| JP | 2019076541 A | 5/2019 |

* cited by examiner

*Primary Examiner* — Nyrobi Celestine
(74) *Attorney, Agent, or Firm* — SPQ IP LLC

(57) ABSTRACT

A method of controlling an ultrasonic probe includes: setting imaging conditions of an ultrasonic probe for acquiring ultrasonic images of a subject; transmitting an ultrasonic beam from the ultrasonic probe towards the subject; receiving, by the ultrasonic probe, an echo from the subject in accordance with the imaging conditions to generate an ultrasonic image of the subject based on the echo received by the ultrasonic probe; identifying the imaging site included in the ultrasonic image; and determining whether to change the imaging conditions based on the identified imaging site. Determining whether to change the imaging conditions includes: identifying a first category from the plurality of categories that corresponds to the identified imaging site; identifying a second category from the plurality of categories that correspond to the set imaging conditions; and maintain the imaging conditions based on the first category and the second category matching.

3 Claims, 22 Drawing Sheets

Ei (E1~En)

EAi

Labeling

Correct answer data

| Category | Parameter set |
|----------|---------------|
| 1 | A1, A2 |
| 2 | B1, B2, B3, B4 |
| 3 | C1, C2, C3 |
| 4 | D1, D2, D3, D4 |
| ⋮ | ⋮ |
| N | N1, N2, ...., Nz |

A1: Parameter set for thyroid gland $(a_{11}, a_{12}, a_{13}, ...., a_{1z})$

A2: Parameter set for carotid artery $(a_{21}, a_{22}, a_{23}, ...., a_{2z})$

B1: Parameter set brachial vein $(b_{11}, b_{12}, b_{13}, ...., b_{1z})$

B2: Parameter set brachial artery $(b_{21}, b_{22}, b_{23}, ...., b_{2z})$

B3: Parameter set lower extremity vein $(b_{31}, b_{32}, b_{33}, ...., b_{3z})$

B4: Parameter set lower extremity artery $(b_{41}, b_{42}, b_{43}, ...., b_{4z})$

Fig. 10

| Category | Parameter set |
|----------|---------------|
| 1 | A1, A2 |
| 2 | B1, B2, B3, B4 |
| 3 | C1, C2, C3 |
| 4 | D1, D2, D3, D4 |
| ⋮ | ⋮ |
| N | N1, N2, ...., Nz |

C1: Parameter set of mammary gland (S)

$(c_{11}, c_{12}, c_{13}, ...., c_{1z})$

C2: Parameter set of mammary gland (M)

$(c_{21}, c_{22}, c_{23}, ...., c_{2z})$

C3: Parameter set of mammary gland (L)

$(c_{31}, c_{32}, c_{33}, ...., c_{3z})$

| Category | Parameter set |
|----------|---------------|
| 1 | A1, A2 |
| 2 | B1, B2, B3, B4 |
| 3 | C1, C2, C3 |
| 4 | D1, D2, D3, D4 |
| ⋮ | ⋮ |
| N | N1, N2, .... ,Nz |

C1: Parameter set of mammary gland (S)

$(c_{11}, c_{12}, c_{13}, ...., c_{1z})$

C2: Parameter set of mammary gland (M)

$(c_{21}, c_{22}, c_{23}, ...., c_{2z})$

C3: Parameter set of mammary gland (L)

$(c_{31}, c_{32}, c_{33}, ...., c_{3z})$

Identified category

1

ULTRASONIC DIAGNOSTIC DEVICE, STORAGE MEDIUM, AND METHOD FOR CHANGING IMAGING CONDITIONS

CROSS-REFERENCE TO RELATED APPLICATION

This application claim priority to Japanese Patent Application No. 2023-088132, which was file on May 29, 2023 at the Japanese Patent Office. The entire contents of the above-listed application are incorporated by reference herein in their entirety.

TECHNICAL FIELD

The disclosure relates to a diagnostic ultrasonic device capable of changing imaging conditions, and a storage medium containing commands to be executed by the diagnostic ultrasonic device.

BACKGROUND

When scanning a subject using an ultrasonic diagnostic device, the user sets the imaging conditions for each imaging site before starting to scan the subject.

Imaging conditions include a variety of parameters. Therefore, a user may have difficulty selecting optimal parameters for each imaging site. Therefore, ultrasonic diagnostic devices are prepared with preset conditions that define the imaging conditions for each imaging site in advance. When imaging a subject, the user can select preset conditions corresponding to the imaging conditions of the subject in order to set the imaging conditions corresponding to the imaging site, thereby acquiring high-quality ultrasonic images. However, it is often difficult for some users to perform an examination of a subject under appropriate imaging conditions because they may not be able to select appropriate preset conditions or may not be able to fully execute parameter adjustments according to the imaging site.

As a method for resolving this problem, a technique is being considered that uses deep learning technology to determine the imaging site of the subject based on the ultrasonic image of the subject, and automatically changes the imaging conditions if the current imaging conditions set by the user are not appropriate for the imaging site of the subject. However, depending on the imaging site of the subject, it may be difficult to identify the site, and it may not be possible to correctly identify the imaging site of the subject. Therefore, as the number of times the imaging conditions are automatically changed increases, the frequency of automatic changes in imaging conditions at timing unintended by the user also increases accordingly.

Therefore, it is desirable to provide technology that can reduce the frequency of automatic changes in imaging conditions at timing unintended by the user.

SUMMARY

According to an aspect, an ultrasonic diagnostic device may include: an ultrasonic probe; and a processor communicating with the ultrasonic probe; wherein the processor performs: setting imaging conditions for acquiring ultrasonic images of the subject; transmitting an ultrasonic beam to the ultrasonic probe and causing the ultrasonic probe to receive an echo from the subject in accordance with the imaging conditions, and generating an ultrasonic image of the subject based on the echo received by the ultrasonic probe; identifying the imaging site included in the ultrasonic image; and determining whether to change the imaging conditions based on the identified imaging site; and the processor determines not to change the imaging conditions if it is determined that the ultrasonic image contains a plurality of imaging sites.

According to an aspect, an ultrasonic diagnostic device may include: an ultrasonic probe; a processor communicating with the ultrasonic probe and a storage device; wherein the processor performs setting imaging conditions for acquiring ultrasonic images of the subject; transmitting an ultrasonic beam to the ultrasonic probe and causing the ultrasonic probe to receive an echo from the subject in accordance with the imaging conditions, and generating an ultrasonic image of the subject based on the echo received by the ultrasonic probe; identifying the imaging site included in the ultrasonic image; and determining whether to change the imaging conditions based on the identified imaging site; and the storage device stores a database containing a plurality of categories, each of which contains a plurality of parameter sets, and the processor performs identifying a first category from the plurality of categories that corresponds to the identified imaging site; identifying a second category from the plurality of categories that corresponds to the set imaging conditions; and determining not to change the imaging conditions when the first category and the second category match.

According to yet another aspect, a recording medium may store commands executable by a processor in communication with an ultrasonic probe, wherein the commands to the processor set the imaging conditions for acquiring ultrasonic images of the subject; transmit an ultrasonic beam to the ultrasonic probe and cause the ultrasonic probe to receive an echo from the subject in accordance with the imaging conditions, and generate an ultrasonic image of the subject based on the echo received by the ultrasonic probe; identify the imaging site included in the ultrasonic image; and determine whether to change the imaging conditions based on the identified imaging site; and the commands to the processor also determine not to change the imaging conditions if it is determined that the ultrasonic image contains a plurality of imaging sites.

According to yet another aspect, a recording medium may store stores commands executable by a processor in communication with an ultrasonic probe, A recording medium, that stores commands executable by a processor in communication with an ultrasonic probe, wherein the commands to the processor: set the imaging conditions for acquiring ultrasonic images of the subject; transmit an ultrasonic beam to the ultrasonic probe and cause the ultrasonic probe to receive an echo from the subject in accordance with the imaging conditions to generate an ultrasonic image of the subject based on the echo received by the ultrasonic probe; identify the imaging site included in the ultrasonic image; and determine whether to change the imaging conditions based on the identified imaging site; wherein determining whether or not to change the imaging conditions includes: identifying a first category from the plurality of categories that corresponds to the identified imaging site; identifying a second category from the plurality of categories that correspond to the set imaging conditions; and determining not to change the imaging conditions when the first category and the second category match.

In one aspect of the present invention, if it is determined that the ultrasonic image contains a plurality of imaging sites, a determination is made not to change the imaging conditions. Thus, the frequency of automatic changes in imaging conditions at timing unintended by the user can be reduced. It also reduces the risk that the currently set imaging conditions will be changed to imaging conditions that are not suitable for the imaging site.

In another aspect of the present invention, parameter sets are distinguished by category, and if the first category corresponding to the determined imaging site and the second category corresponding to the set imaging conditions match, a determination is made to not change the imaging conditions. Thus, the frequency of automatic changes in imaging conditions at timing unintended by the user can be reduced. It also reduces the risk that the currently set imaging conditions will be changed to imaging conditions that are not suitable for the imaging site.

BRIEF DESCRIPTION OF DRAWINGS

FIG. 10 is an explanatory diagram depicting the database according to an embodiment.

DETAILED DESCRIPTION

An embodiment will be described below; however, the disclosure is not limited to the following embodiment.

Figure 1:
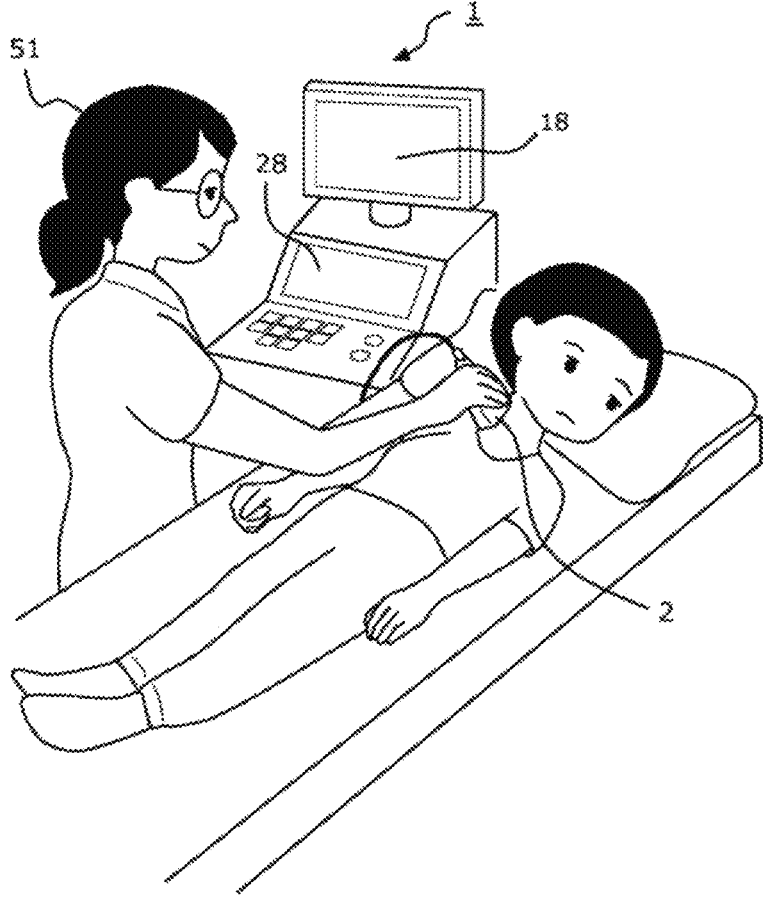
FIG. 1 is a diagram depicting a state of scanning a subject via an ultrasonic diagnostic device 1 according to an embodiment.
Figure 2:
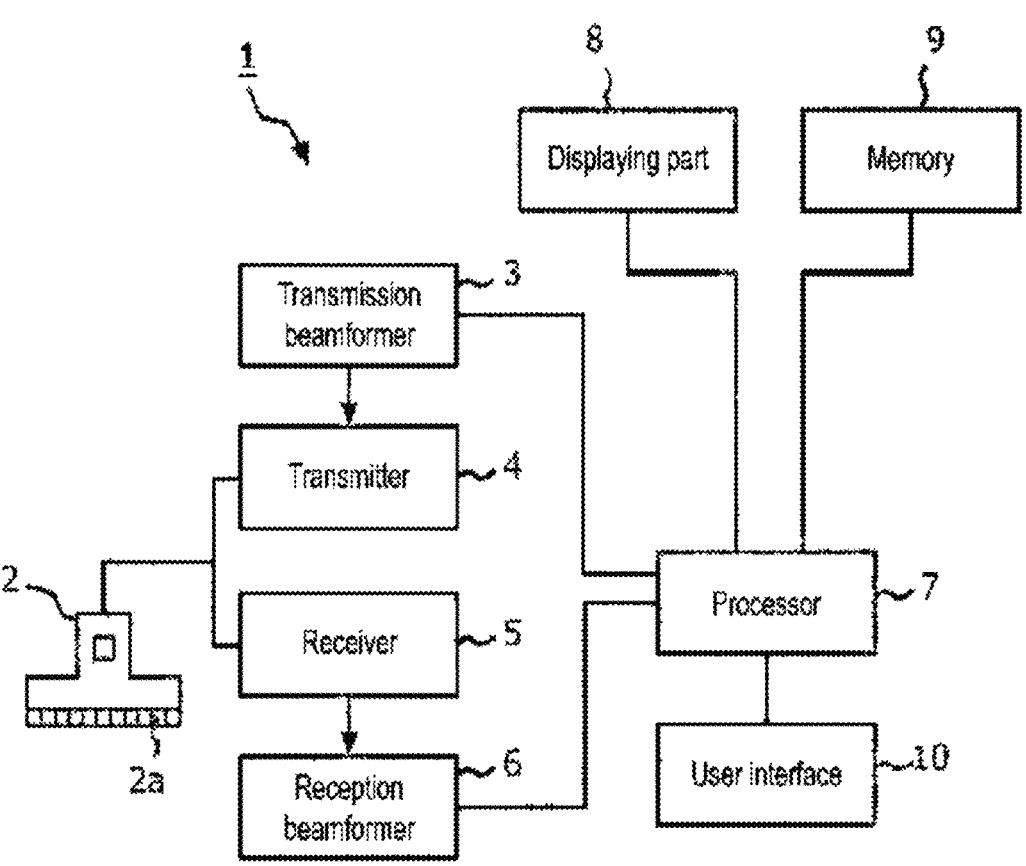
FIG. 2 is a block diagram of the ultrasonic diagnostic device 1 according to an embodiment.

FIG. 1 is a diagram depicting an aspect of scanning a subject via an ultrasonic diagnostic device 1 according to an embodiment, and FIG. 2 is a block diagram of the ultrasonic diagnostic device 1.

The ultrasonic diagnostic device 1 has an ultrasonic probe 2, a transmission beamformer 3, a transmitting apparatus 4, a receiving apparatus 5, a reception beamformer 6, a processor 7, a display 8, a memory 9, and a user interface 10.

The ultrasonic probe 2 has a plurality of vibrating elements 2a arranged in an array. The transmission beamformer 3 and the transmitter 4 drive the plurality of vibrating elements 2a, which are arrayed within the ultrasonic probe 2, and ultrasonic waves are transmitted from the vibrating elements 2a. The ultrasonic waves transmitted from the vibrating element 2a are reflected inside the subject, and a reflection echo is received by the vibrating element 2a. The vibrating elements 2a convert the received echo to an electrical signal and output this electrical signal as an echo signal to the receiver 5. The receiver 5 executes a prescribed process on the echo signal and outputs the echo signal to the reception beamformer 6. The reception beamformer 6 executes reception beamforming on the signal received through the receiver 5 and outputs echo data.

The reception beamformer 6 may be a hardware beamformer or a software beamformer. If the reception beamformer 6 is a software beamformer, the reception beamformer 6 may include a plurality of processors, including one or a plurality of: i) a graphics processing unit (GPU); ii) a microprocessor; iii) a central processing unit (CPU); iv) a digital signal processor (DSP); or v) another type of processor capable of executing logical operations. A processor configuring the reception beamformer 6 may be configured by a processor different from the processor 7 or may be configured by the processor 7.

The ultrasonic probe 2 may include an electrical circuit for performing all or a portion of transmission beamforming and/or reception beamforming. For example, all or a portion of the transmission beamformer 3, the transmitter 4, the receiver 5, and the reception beamformer 6 may be provided in the ultrasonic probe 2.

The processor 7 controls the transmission beamformer 3, the transmitter 4, the receiver 5, and the reception beamformer 6. Furthermore, the processor 7 is in electronic communication with the ultrasonic probe 2. The processor 7 controls which of the vibrating elements 2a is active and the shape of ultrasonic beams transmitted from the ultrasonic probe 2. The processor 7 is also in electronic communication with the display 8 and the user interface 10. The processor 7 can process echo data to generate an ultrasonic image. The term "electronic communication" may be defined to include both wired and wireless communications. The processor 7 may include a central processing unit (CPU) according to one embodiment. According to another embodiment, the processor 7 may include one or more processor, another electronic component that may perform a processing function such as a digital signal processor, a field programmable gate array (FPGA), a graphics processing unit (GPU), another type of processor, and the like. According to another embodiment, the processor 7 may include a plurality of electronic components capable of executing a processing function. For example, the processor 7 may include two or more electronic components selected from a list of electronic components including a central processing unit, a digital signal processor, a field programmable gate array, and a graphics processing unit.

The processor 7 may also include a complex demodulator (not depicted in the drawings) that demodulates RF data. In another embodiment, demodulation may be executed in an earlier step in the processing chain.

Moreover, the processor 7 may generate various ultrasonic images (for example, a B-mode image, color Doppler image, M-mode image, color M-mode image, spectral Doppler image, elastography image, TVI image, strain image, and strain rate image) based on data obtained by processing via the reception beamformer 6. In addition, one or a plurality of modules can generate these ultrasonic images.

An image beam and/or an image frame may be saved, and timing information may be recorded indicating when the data is retrieved to the memory. The module may include, for example, a scan conversion module that performs a scan conversion operation to convert an image frame from a coordinate beam space to display space coordinates. A video processor module may also be provided for reading an image frame from the memory while a procedure is being implemented on the subject and displaying the image frame in real-time. The video processor module may save the image frame in an image memory, and the ultrasonic images may be read from the image memory and displayed on the display 8.

In the present Specification, the term "image" can broadly indicate both a visual image and data representing a visual image. Furthermore, the term "data" can include raw data, which is ultrasonic data before a scan conversion operation, and image data, which is data after the scan conversion operation.

Note that the processing tasks described above handled by the processor 7 may be executed by a plurality of processors.

Furthermore, when the reception beamformer 6 is a software beamformer, a process executed by the beamformer may be executed by a single processor or may be executed by the plurality of processors.

Examples of the display 8 include a LED (Light Emitting Diode) display, an LCD (Liquid Crystal Display), and an organic EL (Electro-Luminescence) display. The display unit 8 displays an ultrasonic image. The display unit 8 includes a display monitor 18 and a touch panel 28, as depicted in FIG. 1. However, the display unit 8 may be configured of a single display unit rather than the display monitor 18 and the touch panel 28. Moreover, two or more display devices may be provided in place of the display monitor 18 and the touch panel 28.

The memory 9 is any known data storage medium. In one example, the ultrasonic image display system includes a non-transitory storage medium and a transitory storage medium. In addition, the ultrasonic image display system may also include a plurality of memories. The non-transitory storage medium is, for example, a non-volatile storage medium such as a Hard Disk Drive (HDD) drive, a Read-Only Memory (ROM), etc. The non-transitory storage medium may include a portable storage medium such as a CD (Compact Disk) or a DVD (Digital Versatile Disk). A program executed by the processor 7 is stored in the non-transitory storage medium. The transitory storage medium is a volatile storage medium such as a Random-Access Memory (RAM).

The memory 9 stores one or a plurality of commands that can be executed by the processor 7. The one or a plurality of commands cause the processor 7 to execute the operations described hereinafter in Embodiments 1 to 4.

Note that the processor 7 may also be configured so as to be able to connect to an external storage device by a wired connection or a wireless connection. In this case, the command causing execution by the processor 7 can be distributed to both the memory 9 and the external storage device for storage.

The user interface 10 can receive input from a user 51. For example, the user interface 10 receives instruction or information input by the user 51. The user interface 10 is configured to include a keyboard (keyboard), a hard key (hard key), a trackball (trackball), a rotary control (rotary control), a soft key, and the like. The user interface 10 may include a touch screen (for example, a touch screen for the touch panel 28) for displaying the soft key and the like. The ultrasonic diagnostic device 1 is configured as described above.

When scanning a subject using an ultrasonic diagnostic device, the user sets the imaging conditions for each imaging site before starting to scan the subject.

Imaging conditions include a variety of parameters. Therefore, a user may have difficulty selecting optimal parameters for each imaging site. Therefore, ultrasonic diagnostic devices are prepared with preset conditions that define the imaging conditions for each imaging site in advance. When imaging a subject, the user can select preset conditions corresponding to the imaging conditions of the subject in order to set the imaging conditions corresponding to the imaging site.

However, it is often difficult for some users to perform an examination of a subject under appropriate imaging conditions because they may not be able to select appropriate preset conditions or may not be able to fully execute parameter adjustments according to the imaging site.

As a method for resolving this problem, a technique is being considered that uses deep learning technology to determine the imaging site of the subject based on the ultrasonic image of the subject, and automatically changes the imaging conditions if the current imaging conditions set by the user are not appropriate for the imaging site of the subject. However, depending on the imaging site of the subject, it may be difficult to identify the site, and it may not be possible to correctly identify the imaging site of the subject. Therefore, as the number of times the imaging conditions are automatically changed increases, the frequency of automatic changes in imaging conditions at timing unintended by the user also increases accordingly.

Therefore, the diagnostic ultrasonic device 1 of the first embodiment is configured to reduce the frequency of automatic changes in imaging conditions at timing unintended by the user. The first embodiment is described below in detail.

Note that in the first embodiment, a trained model is used to deduce the imaging site of the subject, and based on the result of this deduction, a determination is made as to whether the imaging conditions should be changed. Therefore, in the first embodiment, a training phase is performed to generate a trained model, which is suitable for deducing the imaging site of the subject. Therefore, first, a training phase for generating this trained model is described below. Furthermore, after describing the training phase, the method for automatically changing the imaging conditions during the examination of the subject will be described.

(Training Phase)

FIGS. 3 to 6 are explanatory diagrams of the training phase.

In the training phase, first, original images are prepared which form a basis for generating the training image.

Figure 3:
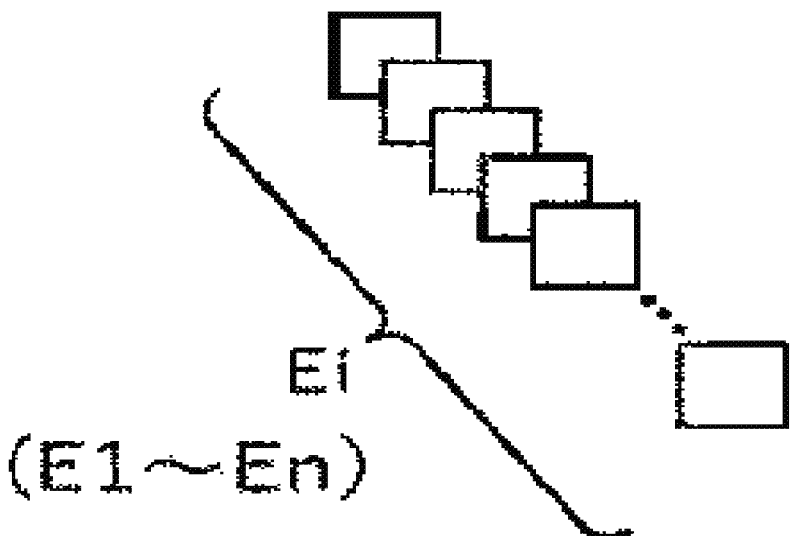
FIG. 3 is a schematic view of an original image according to an embodiment.

FIG. 3 is a schematic view of the original image.

In the first embodiment, a plurality of ultrasonic images Ei (i=1 to n) are prepared as original images. The plurality of ultrasonic images Ei (i=1 to n) are, for example, ultrasonic images acquired at medical facilities such as hospitals or medical equipment manufacturers. These ultrasonic images Ei include images of various imaging sites. The imaging site can be any site that can be subject to ultrasonic diagnosis, such as, but not limited to, the "abdomen", "breast", "carotid artery", "thyroid gland", and "lower extremity". For example, 5,000 to 10,000 examples of original images are prepared.

Figure 4:
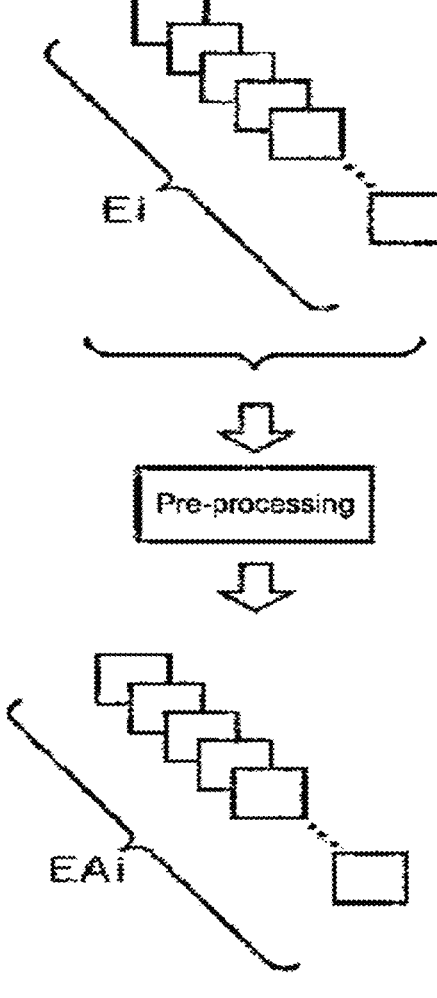
FIG. 4 is an explanatory diagram of pre-processing according to an embodiment.

Next, pre-processing is performed on these original images Ei, as depicted in FIG. 4. This pre-processing includes, for example, image cropping, standardization, normalization, image inversion, image rotation, a magnification percentage change, and an image quality change. An pre-processed original image EAi can be obtained by preprocessing the original image Ei. Each pre-processed original image is used as a training image for creating the trained model.

Figure 5:
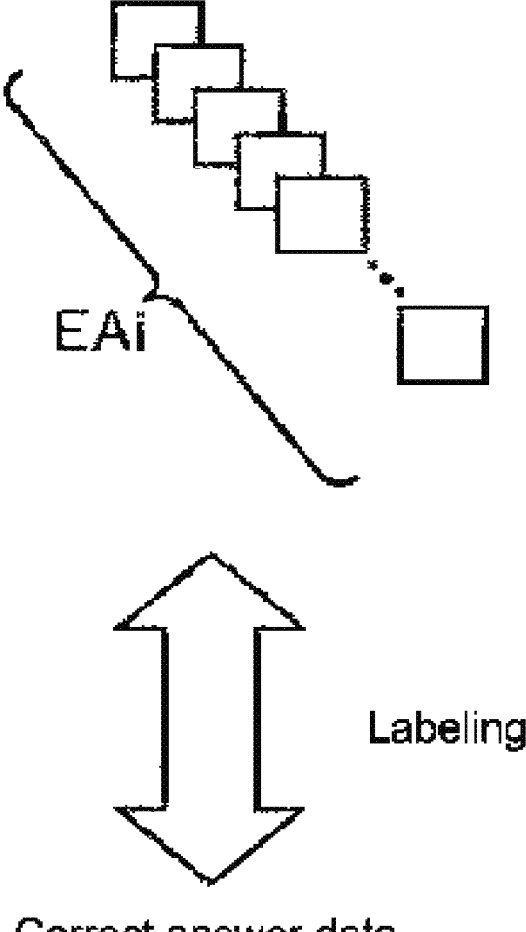
FIG. 5 is an explanatory diagram of leveling the correct data according to an embodiment.

Next, these training data are labelled as correct data (see FIG. 5).

FIG. 5 is a schematic explanatory diagram of correct data labeling.

In Embodiment 1, a plurality of imaging sites targeted for examination via a plurality of the ultrasonic diagnostic devices 1 are used as the correct data.

For example, if the imaging site of the training image is an abdomen, the correct data for the training image will be labeled "abdomen", and if the imaging site of the training image is of a breast, the correct data for the training image will be labeled "breast".

Figure 6:
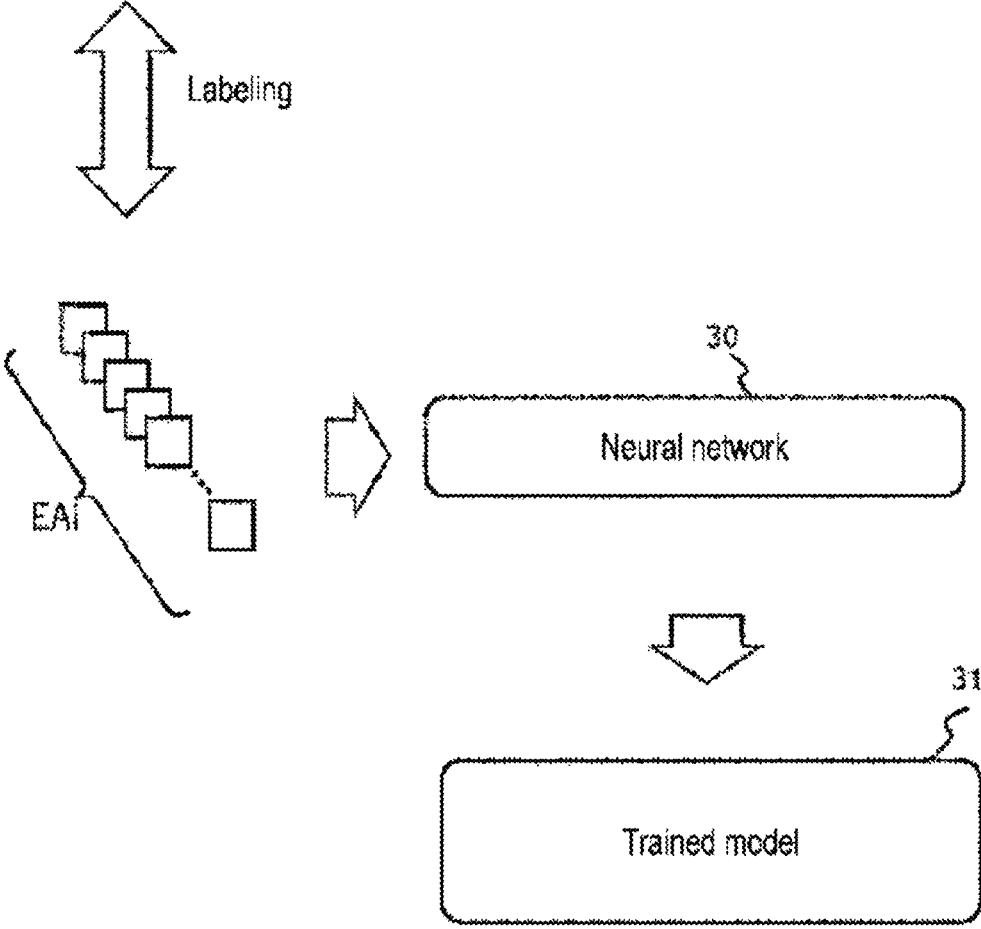
FIG. 6 is a schematic explanatory diagram of a method for creating a trained mode according to an embodiment 1.

Next, the trained model is created using the above training data. FIG. 6 is a schematic explanatory diagram of a method for creating a trained model.

A trained model 31 can be created by training a neural network 30 with the training images described above. The trained model 31 is stored in memory or external storage device. The trained model 31 can be created using any training algorithm used in AI learning, machine learning, or deep learning. For example, the trained model 31 may be created by supervised or unsupervised learning.

In the first embodiment, the trained model 31 is used to determine whether to automatically change the imaging conditions. An example of the determination method is described below with reference to FIG. 7.

Figure 7:
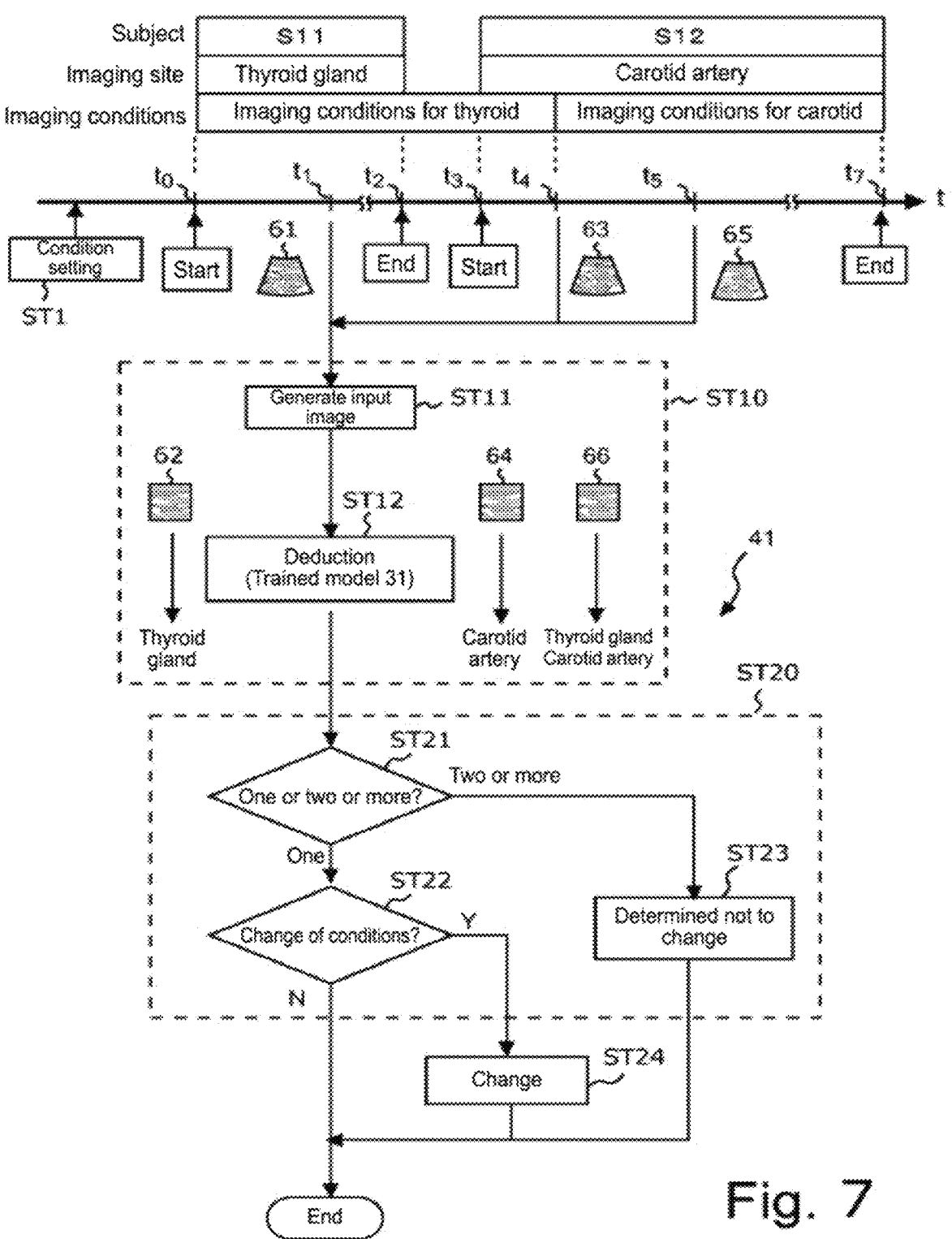
FIG. 7 is a diagram depicting an example of a flowchart executed during an examination of a subject according to an embodiment.

FIG. 7 is a diagram depicting an example of a flowchart executed during an examination of a subject.

In step ST1, the user 51 (for example, physician, ultrasonic technician) guides the subject to the examination room and places the subject on the examination bed. The user 51 operates the user interface 10 (see FIG. 2) to enter patient information, set imaging conditions for acquiring ultrasonic images of the subject, and make other necessary settings. The imaging conditions include any conditions related to the acquisition of ultrasonic images, such as the conditions for transmitting the ultrasonic beam, the conditions for receiving echoes from the subject, and the data processing conditions used to create an ultrasonic image based on the received echoes.

Here, the imaging site of the subject is set to the "thyroid gland". Thus, the user 51 sets the imaging conditions for the thyroid gland.

When the user 51 is ready for the examination, the user begins examining the subject. In FIG. 7, the inspection start point is indicated as t0.

In FIG. 7, "subject", "imaging site", and "imaging conditions" are indicated on the time axis. The "subject" represents the subject being examined, "imaging site" represents the imaging site of the subject, and "imaging conditions" represents the imaging conditions set for the ultrasonic diagnostic device. For example, at time to when the examination starts, the diagram depicts that the "subject" is subject S11, the "imaging site" is the thyroid gland, and the "imaging conditions" are the V1 imaging conditions for the thyroid gland.

The user 51 operates the probe and scans the subject S11 while pressing the ultrasonic probe 2 against an imaging site of the subject S11. Here, the imaging site of the subject S11 is the thyroid gland, so the user 51 presses the ultrasonic probe 2 against the neck of the subject S11 to perform the examination. The ultrasonic probe 2 transmits an ultrasonic wave and receives an echo reflected from within the subject S11. The received echo is converted to an electrical signal, and this electrical signal is output as an echo signal to the receiving apparatus 5 (see FIG. 2). The receiver 5 executes a prescribed process on the echo signal and outputs the echo signal to the reception beamformer 6. The reception beamformer 6 executes reception beamforming on the signal received through the receiver 5 and outputs echo data.

The processor 7 generates an ultrasonic image based on the echo data.

The user 51 can review the generated ultrasonic images or save the ultrasonic images if necessary. Furthermore, the user 51 continues to perform the examination of the subject S11.

On the other hand, the processor 7 periodically executes a process 41 after the examination of subject S11 starts at time t0 to determine whether the imaging conditions should be changed and to automatically change the imaging conditions as necessary. In this embodiment, the first process 41 is executed at time t1 after the inspection start time to. The process 41 is described below.

When process 41 is initiated, first, in step ST10, the processor 7 identifies the imaging site in the ultrasonic image acquired between time points t0 and t1. The identifying step ST10 will be described below.

First, in step ST11, the processor generates an input image 62 for inputting to the trained model 31 based on the ultrasonic image 61 acquired between time t0 and time t1. Specifically, the processor 7 generates an input image 62 by preprocessing the ultrasonic image 61. This pre-processing is basically the same as the pre-processing executed when generating training images for the trained model 31. The input image 62 for inputting to the trained model 31 can be generated by executing pre-processing.

If one ultrasonic image 61 is acquired between time t0 and time t1, the processor 7 generates an input image 62 in order to input to the trained model 31 based on the ultrasonic image 61.

On the other hand, if a plurality of ultrasonic images have been acquired between time t0 and time t1, the processor 7 selects one of the plurality of ultrasonic images 61 and generates an input image 62 for inputting to the trained model 31 based on the selected ultrasonic image 61. If a plurality of ultrasonic images are acquired between time t0 and time t1, the processor 7 can typically select the last acquired ultrasonic image or the ultrasonic image acquired immediately before time t1 when the process 41 is initiated as the ultrasonic image 61. After the input image 62 is generated, the process proceeds to step ST12.

Figure 8:
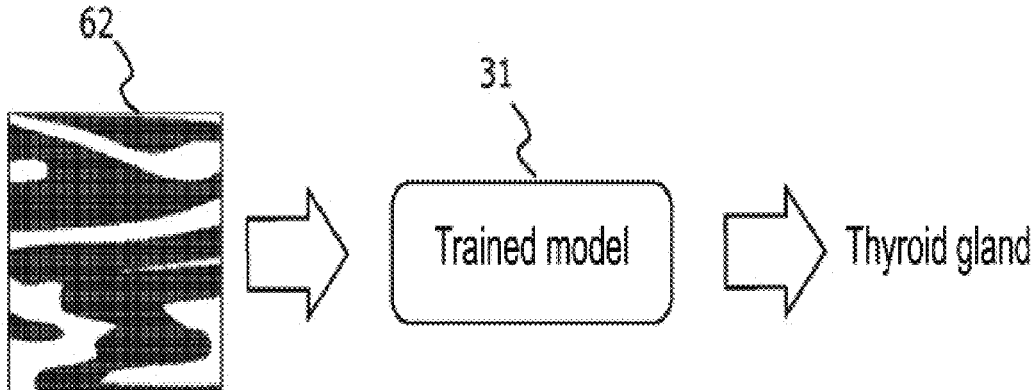
FIG. 8 is an explanatory diagram depicting deduction of the imaging site according to an embodiment.

In step ST12, the processor 7 deduces a location indicated by the input image 62 using the trained model 31 (see FIG. 8).

FIG. 8 depicts the deduction of the imaging site.
The processor 7 inputs the input image 62 into the trained model 31 and uses the trained model 31 to deduce the sites contained in the input image 62. In the deduction step, the processor 7 calculates the probability that each imaging site is included in the input image 62. Furthermore, the processor 7 then deduces the imaging site in the input image 62 based on the probability calculated for each imaging site.

The processor 7 compares the probability calculated for each imaging site with a threshold value. The threshold value is a reference value for determining whether each imaging site is included in the input image 62. In this embodiment, if the probability of an imaging site is greater than a threshold value, it is deduced that the site is included in the input image 62. For example, if only the thyroid gland has a probability of exceeding the threshold among the plurality of imaging sites, the processor 7 deduces that the imaging site included in input image 62 is the thyroid gland, as depicted in FIG. 8. On the other hand, it may be deduced that the input image 62 contains a plurality of imaging sites (see FIG. 9).

Figure 9:
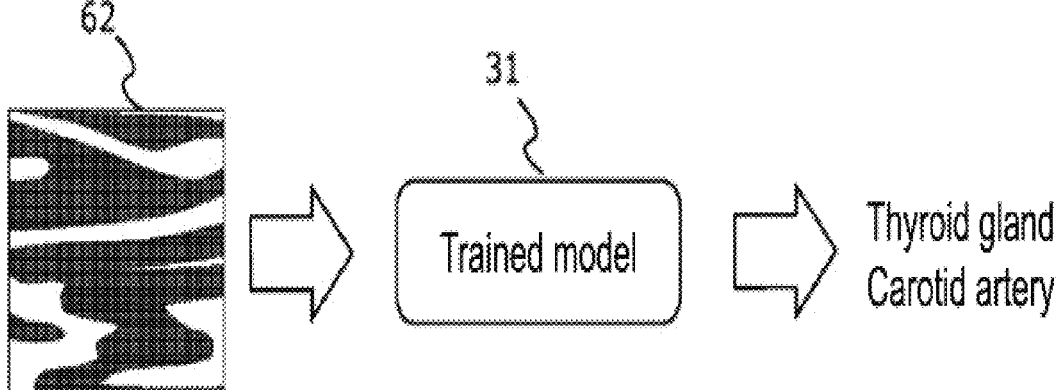
FIG. 9 is an explanatory diagram of an example where it is deduced that the input image 62 contains a plurality of imaging sites according to an embodiment.

FIG. 9 depicts an example where it is deduced that the input image 62 contains a plurality of imaging sites.
For example, if the input image 62 contains both thyroid and carotid sites, and the probability for the thyroid and the carotid artery exceed a threshold value, the processor 7 deduces that the input image 62 contains two imaging sites, namely, the thyroid gland and the carotid artery.

It can be assumed that the trained model 31 outputs "thyroid gland" as the deduction result, as depicted in FIG. 8. Therefore, in step ST12, the processor 7 deduces that the imaging site is the thyroid gland. After deducing the imaging site, the process proceeds to step ST20.

In step ST20, the processor 7 determines whether to change the imaging conditions based on the deduced imaging site. Step ST20 will be described below in detail.

First, in step ST21, the processor 7 determines whether the number of imaging sites deduced in the input image 62 is one or two or more. If the number of imaging sites is one, the process proceeds to step ST22, and if the number of imaging sites is two or more, the process proceeds to step ST23. Here, it is deduced that the input image 62 contains only the thyroid gland, so the processor 7 determines that there is one imaging site in the input image 62. Therefore, the process proceeds to step ST22.

In step ST22, the processor 7 determines whether to change the imaging conditions. The processor 7 determines whether the currently set imaging conditions are those corresponding to the imaging site deduced in step ST12. If the currently set imaging conditions are those corresponding to the imaging site deduced in step ST12, the processor 7 determines not to change the imaging conditions and terminates the process 41. On the other hand, if the currently set imaging conditions are not the imaging conditions corresponding to the imaging site deduced in step ST12, the process proceeds to step ST24 and the processor 7 makes a determination to change the imaging conditions.

At time t1, the set imaging condition is V1 for the thyroid gland. On the other hand, the imaging site deduced in step ST12 is the thyroid gland. Therefore, the currently set imaging conditions V1 are those corresponding to the imaging site (thyroid gland) deduced in step ST12, so the processor 7 determines not to change the imaging conditions and terminates the process 41.

On the other hand, the user 51 continues the examination of the subject S11 while operating the ultrasonic probe 2 after time t1. The processor 7 periodically executes the above process 41 during the examination of the subject S11. It can be assumed that the imaging of the thyroid gland of the subject S11 is completed without any change in imaging conditions. The end of the thyroid gland imaging of subject S11 is indicated by "t2". After the examination of the subject S11 is completed, the next subject S12 is prepared for examination.

The case where the imaging site of a new subject S12 is different from that of the immediately preceding subject S11 is described below. Here, the case where the imaging site of the immediately preceding subject S11 is the thyroid gland was described, but the imaging site of the new subject S12 is the carotid artery.

The user 51 prepares for the examination of the carotid artery of a new subject S12 after completing the thyroid gland examination of the immediately preceding subject S11. In this case, the imaging site is changed from the thyroid gland to the carotid artery, so the user 51 must change the imaging conditions from V1 for the thyroid gland to V2 for the carotid artery. In the following, however, the case is considered in which the user 51 initiates an examination of the carotid artery of a new subject S12 without changing the imaging conditions.

At time t3, the user 51 begins examining the carotid artery of the new subject S12. The user 51 starts examining the carotid artery of the subject S12 at time t3, but since the imaging conditions have not been changed, the set imaging conditions remain the same as the V1 imaging conditions for the thyroid gland. Therefore, user 51 starts the examination of the carotid artery of subject S12 with the imaging condition V1 for the thyroid gland.

On the other hand, the processor 7 periodically executes the process 41 after the examination of the carotid artery of subject S12 begins at time t3. The present embodiment describes the case where the process 41 is executed at time t4 after time t3.

When process 41 is initiated, first, in step ST10, the processor 7 identifies the imaging site in the ultrasonic image acquired between time points t3 and t4. The identifying step ST10 will be described below.

First, in step ST11, the processor 7 generates an input image 64 for inputting to the trained model 31 by preprocessing the ultrasonic image 63 acquired between time t3 and time t4.

If one ultrasonic image 63 is acquired between time t3 and time t4, the processor 7 can generate an input image 64 in order to input to the trained model 31 by preprocessing the ultrasonic image 63. On the other hand, if a plurality of ultrasonic images have been acquired between time t3 and time t4, the processor 7 selects one of the plurality of ultrasonic images 63 and can generate an input image 64 for inputting to the trained model 31 based on the selected ultrasonic image 63. If a plurality of ultrasonic images have been acquired between time t3 and time t4, the processor 7 can typically select the last ultrasonic image acquired between time t3 and time t4 (the ultrasonic image acquired just before time t4) as the ultrasonic image 63.

After the input image 64 is generated, the process proceeds to step ST12.

In step ST12, the processor 7 deduces a location indicated by the input image 64 using the trained model 31.

The processor 7 inputs the input image 64 into the trained model 31 and uses the trained model 31 to deduce the sites contained in the input image 64. It can be assumed that the processor 7 has deduced that the input image 64 contains a carotid artery, as depicted in FIG. 7. After deducing the imaging site, the process proceeds to step ST20.

In step ST20, the processor 7 determines whether to change the imaging conditions based on the deduced imaging site. Step ST20 will be described below in detail.

First, in step ST21, the processor 7 determines whether the number of imaging sites deduced in the input image 64 is one or two or more. If the number of imaging sites is one, the process proceeds to step ST22, and if the number of imaging sites is two or more, the process proceeds to step ST23. Here, it is deduced that the input image 64 contains only the carotid artery, so the processor 7 determines that there is one imaging site in the input image 64. Therefore, the process proceeds to step ST22.

In step ST22, the processor 7 determines whether to change the imaging conditions. The processor 7 determines whether the currently set imaging conditions are those corresponding to the imaging site deduced in step ST12. If the currently set imaging conditions are those corresponding to the imaging site deduced in step ST12, the processor 7 determines not to change the imaging conditions and terminates the process 41. On the other hand, if the currently set imaging conditions are not the imaging conditions corresponding to the imaging site deduced in step ST12, the process proceeds to step ST24 and the processor 7 makes a determination to change the imaging conditions.

At time t4, the set imaging condition is V1 for the thyroid gland. On the other hand, the imaging site deduced in step ST12 is the carotid artery. Therefore, the currently set imaging conditions are not the imaging conditions corresponding to the imaging site (carotid artery) deduced in step ST12. Therefore, processor 7 makes a determination to change the imaging conditions and the process proceeds to step ST24 to change the imaging conditions from V1 for the thyroid gland to V2 for the carotid artery. Therefore, immediately after the flow of process 41 is completed (immediately after time t4), the imaging conditions are automatically changed from imaging condition V1 for the thyroid gland to imaging condition V2 for the carotid artery.

Therefore, the user 51 started imaging the carotid artery of subject S12 without changing the imaging conditions to the V2 imaging conditions for the carotid artery, but the processor 7 sets the imaging conditions to the V2 imaging conditions for the carotid artery immediately after time t4. Therefore, even if the user 51 forgets to change the imaging conditions, after the processor 7 changes the imaging conditions, the user 51 can still acquire high-quality images of the carotid artery because the user can image the carotid artery of the subject S12 according to the V2 imaging conditions for the carotid artery.

The user 51 continues to examine the carotid artery of the subject S12 while operating the ultrasonic probe 2 after time t4, and the processor 7 periodically executes the above process 41. Furthermore, an example is described where the processor 7 executes the process 41 again at time t5.

When process 41 is initiated, first, in step ST10, the processor 7 identifies the imaging site in the ultrasonic image acquired between time t4 and t5. The identifying step ST10 will be described below.

First, in step ST11, the processor generates an input image 66 for inputting to the trained model 31 by preprocessing the ultrasonic image 65 acquired between time t4 and time t5.

If one ultrasonic image 65 is acquired between time t4 and time t5, the processor 7 can generate an input image 66 in order to input to the trained model 31 by preprocessing the ultrasonic image 65. On the other hand, if a plurality of ultrasonic images have been acquired between time t4 and time t5, the processor 7 selects one of the plurality of ultrasonic images 65 and can generate an input image 66 for inputting to the trained model 31 based on the selected ultrasonic image 65. If a plurality of ultrasonic images have been acquired between time t4 and time t5, the processor 7 can typically select the last ultrasonic image acquired between time t4 and time t5 (the ultrasonic image acquired just before time t5) as the ultrasonic image 65.

After the input image 66' is generated, the process proceeds to step ST12.

In step ST12, the processor 7 deduces a location indicated by the input image 66 using the trained model 31.

The processor 7 inputs the input image 66 into the trained model 31 and uses the trained model 31 to deduce the sites contained in the input image 66. In the deduction step, the processor 7 calculates the probability that each imaging site is included in the input image 66. Furthermore, the processor 7 then deduces the imaging site in the input image 66 based on the probability calculated for each imaging site.

It can be assumed that the thyroid gland and carotid artery probabilities exceed the threshold value. Thus, in this case, the processor 7 deduces that the input image 66 contains the thyroid gland and the carotid artery, as depicted in FIG. 7. After deducing the imaging site, the process proceeds to step ST20.

In step ST20, step ST21 is performed first.

In step ST21, the processor 7 determines whether the number of imaging sites deduced in the input image 66 is one or two or more. If the number of imaging sites is one, the process proceeds to step ST22, and if the number of imaging sites is two or more, the process proceeds to step ST23. Here, it is deduced that the input image 66 contains the thyroid gland and the carotid artery, so the processor 7 determines that there is two or more imaging sites in the input image 66. If it is determined that the input image 66 contains two or more imaging sites, the process proceeds to step ST23 and processor 7 makes a determination not to change the imaging conditions. The reason is described below.

It is deduced that the input image 66 contains two imaging sites, namely the thyroid gland and the carotid artery. Therefore, when attempting to change the imaging conditions, the processor 7 must first identify whether the imaging site of subject S12 is the thyroid gland or the carotid artery. However, at time t5, user 51 is examining the carotid artery, so if the processor 7 identifies the current imaging site as the thyroid gland and, as a result, automatically changes the imaging conditions to the imaging conditions for the thyroid gland, the user 51 will continue imaging the carotid artery of the subject S12 under the imaging conditions for the thyroid gland. Therefore, if the processor 7 had not changed the imaging conditions, the user 51 would have been able to continue imaging the carotid artery of subject S12 under the imaging conditions for the carotid artery. However, since the processor 7 did change the imaging conditions, the user 51 will continue to image the carotid artery of the subject S12 using the imaging conditions of the thyroid gland.

Therefore, in order to prevent such a problem from occurring in the present embodiment, the processor 7 makes a determination not to change the imaging conditions in step ST23 and terminates the flow of process 41 if it is deduced that the input image 66 contains a plurality of imaging sites. Therefore, if it is deduced that the input image 66 contains a plurality of imaging sites, the processor 7 does not change the imaging conditions, thus avoiding the risk that the currently set imaging conditions will be automatically changed to those for another imaging site not intended by the user 51.

On the other hand, the user 51 continues to examine the carotid artery of the subject S12 while operating the ultrasonic probe 2 after time t5, and the processor 7 periodically executes the above process 41. Furthermore, when all images necessary for the diagnosis of the carotid artery of the subject S12 have been acquired, the examination is completed (at time t7).

If the input image contains a plurality of imaging sites, the process 41 is terminated without changing the imaging conditions. Thus, the frequency of automatic changes in imaging conditions at timing unintended by the user 51 can be reduced. This also avoids the risk of the current imaging conditions being automatically changed to imaging conditions for a different imaging site not intended by the user 51.

(2) Embodiment 2

The second embodiment describes an example of classifying the parameter sets included in the imaging conditions of an imaging site into a plurality of categories and determining whether to change the imaging conditions based on the results of the classification.

In the second embodiment, a database for managing a plurality of categories is stored in the memory (or external storage device) of the ultrasonic diagnostic device. The second embodiment will be described by first describing the database that manages a plurality of categories. After this description, the flow for automatically changing the imaging conditions will be described.

FIG. 10 depicts the database stored in the memory (or external storage device) of the ultrasonic diagnostic device. The database contains a plurality of categories 1 to N. Each category contains a plurality of sets of parameters. Each parameter set contains a plurality of parameters that are set when the imaging site is imaged. Each parameter set is classified into one of a plurality of categories 1 to N, based on whether the anatomical features of the imaging site are similar and/or whether the parameter values are similar. Categories 1 through N of the database are described below, focusing on categories 1 and 2 of categories 1 through N. An explanatory diagram of the parameter sets for categories 1 and 2 is depicted in the right half of FIG. 10.

Category 1 includes thyroid gland parameter set A1 and carotid artery parameter set A2.

The thyroid parameter set A1 contains a plurality of parameters that are set during thyroid gland imaging. In FIG. 10, the parameters included in the thyroid gland parameter set A1 are indicated by $(a_{11}, a_{12}, a_{13}, \ldots a_{1z})$. These parameters an to $a_{1z}$ include, for example, frequency and depth.

The carotid artery parameter set A2 contains a plurality of parameters that are set when imaging the carotid artery. In FIG. 10, the parameters included in the carotid artery parameter set A2 are indicated by $(a_{21}, a_{22}, a_{23}, \ldots a_{2z})$. These parameters $a_{21}$ to $a_{2z}$ include, for example, frequency and depth.

Furthermore, category 2 also includes brachial vein parameter set B1, brachial artery parameter set B2, lower extremity vein parameter set B3, and lower extremity artery parameter set B4.

The brachial vein parameter set B1 contains a plurality of parameters that are set when imaging the brachial vein. In FIG. 10, the parameters included in the brachial vein parameter set B1 are indicated by $(b_{11}, b_{12}, b_{13}, \ldots b_{1z})$. These parameters $b_{11}$ to $b_{1z}$ include, for example, frequency and depth.

The brachial artery parameter set B2 contains a plurality of parameters that are set when imaging the brachial artery. In FIG. 10, the parameters included in the brachial artery parameter set B2 are indicated by $(b_{21}, b_{22}, b_{23}, \ldots b_{2z})$. These parameters $b_{21}$ to $b_{2z}$ include, for example, frequency and depth.

The lower extremities vein parameter set B3 contains a plurality of parameters that are set when imaging the lower extremity veins. In FIG. 10, the parameters included in the lower extremity vein parameter set B3 are indicated by $(b_{31}, b_{32}, b_{33}, \ldots b_{3z})$. These parameters $b_{31}$ to $b_{3z}$ include, for example, frequency and depth.

The lower extremity artery parameter set B4 contains a plurality of parameters that are set when imaging the lower extremity arteries. In FIG. 10, the parameters included in the lower extremity artery parameter set B4 are indicated by $(b_{41}, b_{42}, b_{43}, \ldots b_{4z})$. These parameters $b_{41}$ to $b_{4z}$ include, for example, frequency and depth.

Furthermore, the other categories 3 through N are also included in parameter sets that include a plurality of parameters, although detailed descriptions are omitted.

The above parameters may be predetermined as preset conditions before examining the subject, or they may be set manually by the user 51 before examining the subject.

The second embodiment describes an example of using the above categories 1 to N registered in the database to determine whether or not to change the imaging conditions during examination of a subject.

Figure 11:
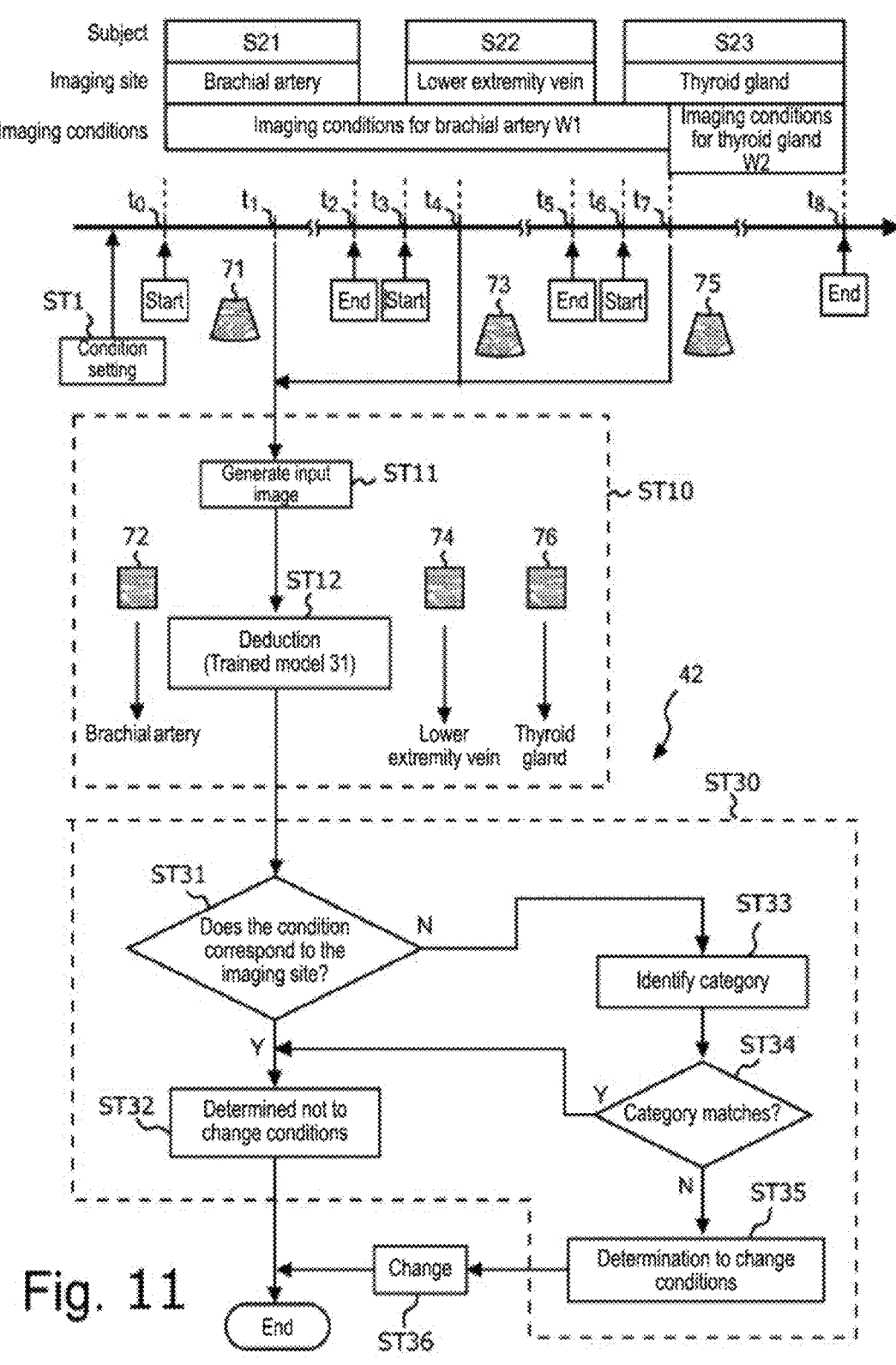
FIG. 11 is a diagram depicting an example of a flowchart executed during an examination of a subject according to an embodiment.

FIG. 11 is a diagram depicting an example of a flowchart executed during an examination of a subject.

In step ST1, the user 51 leads the subject to the examination room and places the subject on the examination bed. The user 51 operates the user interface 10 (see FIG. 2) to enter patient information, set imaging conditions for acquiring ultrasonic images of the subject, and make other necessary settings. Here, the imaging site of the subject is set to the "brachial artery". Therefore, the user 51 sets the imaging conditions for the brachial artery.

When the user 51 is ready for the examination, the user begins examining the subject. In FIG. 11, the inspection start point is indicated as t0.

In FIG. 11, "subject", "imaging site", and "imaging conditions" are depicted on the time axis. The "subject" represents the subject being examined, "imaging site" represents the imaging site of the subject, and "imaging conditions" represents the imaging conditions set for the ultrasonic diagnostic device. For example, at time to when the examination starts, the diagram depicts that the "subject" is subject S21, the "imaging site" is the brachial artery, and the "imaging conditions" are the V1 imaging conditions for the brachial artery.

The user 51 operates the probe while pressing the ultrasonic probe 2 against the upper arm of the subject S21 to examine the subject S21. The ultrasonic probe 2 transmits an ultrasonic wave and receives an echo reflected from within the subject S21. The received echo is converted to an electrical signal, and this electrical signal is output as an echo signal to the receiving apparatus 5 (see FIG. 2). The receiver 5 executes a prescribed process on the echo signal and outputs the echo signal to the reception beamformer 6. The reception beamformer 6 executes reception beamforming on the signal received through the receiver 5 and outputs echo data.

The processor 7 generates an ultrasonic image based on the echo data.

The user 51 can review the generated ultrasonic images or save the ultrasonic images if necessary. Furthermore, the user 51 continues to perform the examination of the subject.

On the other hand, the processor 7 periodically executes a process 42 after the examination of subject S21 starts at time t0 to determine whether the imaging conditions should be changed and to automatically change the imaging conditions as necessary. In the present embodiment, the first process 42 is executed at time t1 after the inspection start time to. The process 42 is described below.

When process 42 is initiated, first, in step ST10, the processor 7 identifies the imaging site in the ultrasonic image acquired between time t0 and t1. The identifying step ST10 will be described below.

First, in step ST11, the processor 7 generates an input image 72 for inputting to the trained model 31 by preprocessing the ultrasonic image 71 acquired between time t0 and time t1.

If one ultrasonic image 71 is acquired between time to and time t1, the processor 7 generates an input image 72 in order to input to the trained model 31 based on the ultrasonic image 71. The processor 7 generates the input image 72, for example, by preprocessing the ultrasonic image 71 acquired just before time t1. After the input image 72 is generated, the process proceeds to step ST12.

In step ST12, the processor 7 deduces a location indicated by the input image 72 using the trained model 31.

The processor 7 inputs the input image 72 into the trained model 31 and uses the trained model 31 to deduce the sites contained in the input image 72. In the deduction step, the processor 7 calculates the probability that each imaging site is included in the input image 72. Furthermore, the processor 7 then deduces the imaging site in the input image 72 based on the probability calculated for each imaging site.

It can be assumed that the brachial artery probability exceeds the threshold value. Therefore, the processor 7 deduces that the imaging site included in the input image 72 is the brachial artery. After deducing the imaging site, the process proceeds to step ST30.

In step ST30, the processor 7 determines whether to change the imaging conditions based on the deduced imaging site. Step ST30 will be described below in detail.

First, in step ST31, the processor 7 determines whether the currently set imaging conditions are those corresponding to the imaging site deduced in step ST12. If the currently set imaging conditions are the imaging conditions corresponding to the imaging site deduced in step ST12, the process proceeds to step ST32, but if the currently set imaging conditions are not the imaging conditions corresponding to the imaging site deduced in step ST12, the process proceeds to step ST33.

At time t1, the set imaging condition is the imaging condition for the brachial artery. On the other hand, the imaging site deduced in step ST12 is the brachial artery. Therefore, the currently set imaging conditions are the imaging conditions corresponding to the imaging site (brachial artery) deduced in step ST12. Therefore, proceeding to step ST32, the processor 7 makes a determination not to change the imaging conditions, and terminates the process 42.

On the other hand, the user 51 continues the examination of the subject S21 while operating the ultrasonic probe 2 after time t1. The processor 7 periodically executes the above process 42 during the examination of the subject S21. It can be assumed that the imaging of the brachial artery of the subject S21 is completed without any change in imaging conditions. The end of the examination of the brachial artery of the subject S21 is indicated by "t2". After the examination of the subject S21 is completed, the next new subject S22 is prepared for examination.

The case where the imaging site of a new subject S22 is different from that of the immediately preceding subject S21 is described below. Here, the case where the imaging site of the immediately preceding subject S21 is the brachial artery was described, but the imaging site of the new subject S22 is the lower extremity veins.

The user 51 prepares for the examination of the lower extremity vein of a new subject S22 after completing the brachial artery examination of the immediately preceding subject S21. In this case, the imaging site is changed from the brachial artery to the lower extremity vein, so the user 51 must change the imaging conditions from imaging conditions for the brachial artery to the imaging conditions for the lower extremity vein. In the following, however, the case is considered in which the user 51 initiates an examination of the lower extremity vein of a new subject S22 without changing the imaging conditions.

The user 51 initiates the examination of the lower extremity veins of the new subject S22. Here, the time of disclosure of the examination of the lower extremity vein of a new subject S22 is indicated to be at t3.

The user 51 starts examining the lower extremity vein of the subject S22 at time t3, but since the imaging conditions have not been changed, the set imaging conditions remain the same as the W1 imaging conditions for the brachial artery. Therefore, user 51 starts the examination of the lower extremity vein of the new subject S22 with the imaging condition W1 for the brachial artery.

On the other hand, the processor 7 periodically executes the process 42 after the examination of the lower extremity vein of the new subject S22 begins at time t3. The present embodiment describes the case where the process 42 is executed at time t4 after time t3.

First, in step ST11, the processor 7 generates an input image 74 for inputting to the trained model 31 by preprocessing the ultrasonic image 73 acquired between time t3 and time t4. The processor 7 generates the input image 74, for example, by preprocessing the ultrasonic image 73 acquired just before time t4. After the input image 74 is generated, the process proceeds to step ST12.

In step ST12, the processor 7 deduces a location indicated by the input image 74 using the trained model 31.

The processor 7 inputs the input image 74 into the trained model 31 and uses the trained model 31 to deduce the sites contained in the input image 74. It can be assumed that the processor 7 has deduced that the input image 74 contains a lower extremity vein, as depicted in FIG. 11. After deducing the imaging site, the process proceeds to step ST30.

In step ST30, the processor 7 determines whether to change the imaging conditions based on the deduced imaging site. Step ST30 will be described below in detail.

First, in step ST31, the processor 7 determines whether the currently set imaging conditions are those corresponding to the imaging site deduced in step ST12. At time t4, the set imaging condition is the imaging condition for the brachial artery. On the other hand, the imaging site deduced in step ST12 is the lower extremity artery. Therefore, at time t4, the set imaging conditions (imaging conditions for the brachial artery) are not the imaging conditions corresponding to the imaging site (lower extremity vein) deduced in step ST12, so the process proceeds to step ST33.

Figure 12:
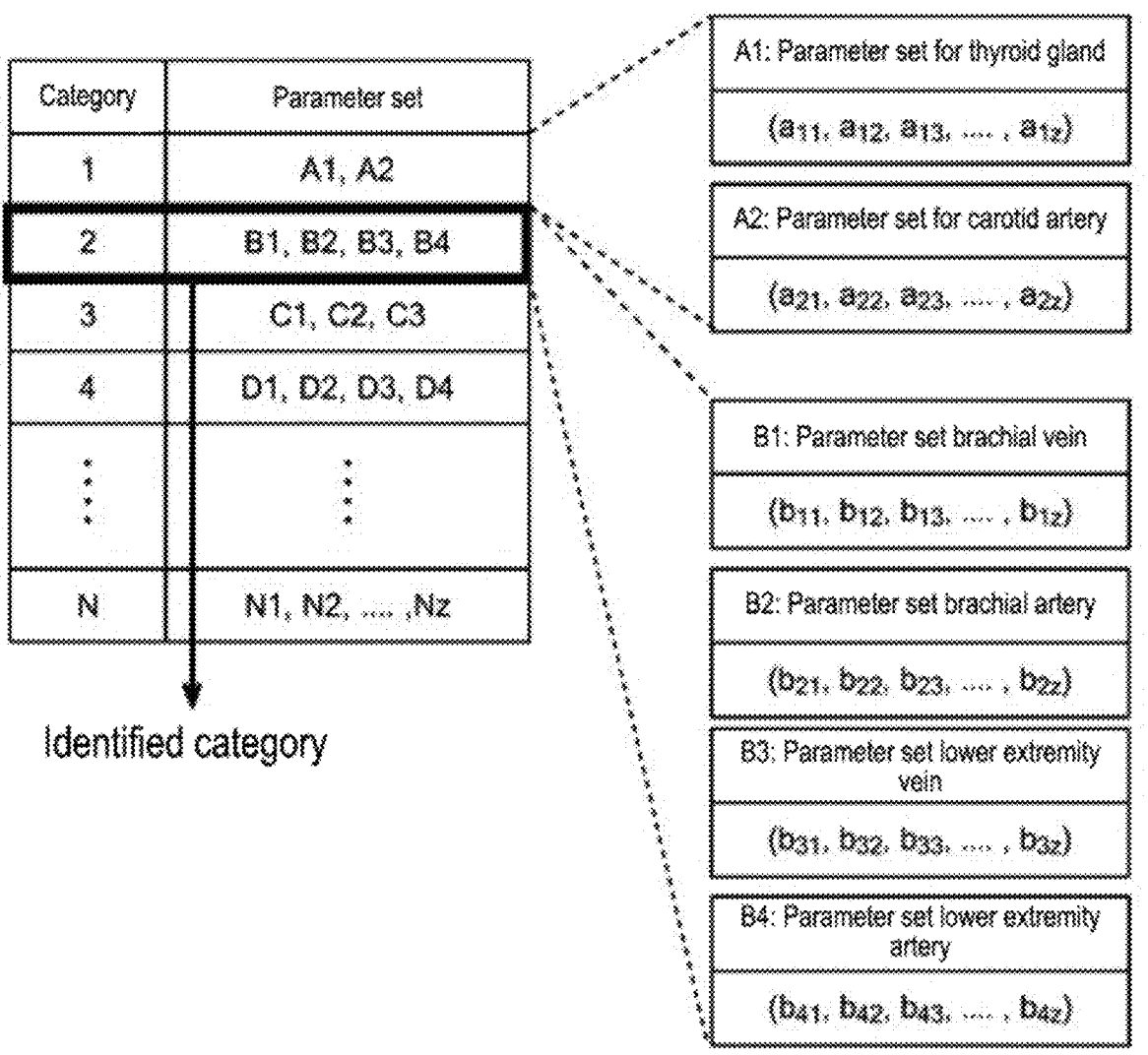
FIG. 12 is an explanatory diagram of step ST33 according to an embodiment.

FIG. 12 is an explanatory diagram of step ST33.
In step ST33, the processor 7 identifies the category corresponding to the deduced imaging site from among the plurality of categories 1 to N registered in the database. Here, the deduced imaging site is the "lower extremity vein", so the processor 7 identifies category 2, which includes the parameter set of the lower extremity vein, from among the plurality of categories 1 to N.

Next, the processor 7 identifies the category corresponding to the currently set imaging conditions from among the plurality of categories 1 to N registered in the database. Here, the currently set imaging conditions are for the brachial artery, so the processor 7 identifies category 2, which contains the parameter set for the brachial artery, from among the plurality of categories 1 to N. After identifying category 2, the process proceeds to step ST34.

In step ST34, the processor 7 determines whether the two categories identified in step ST33 match. If the categories match, the process proceeds to step ST32, while if the categories do not match, the process proceeds to step ST35. Here, the identified categories match (category 2), so the process proceeds to step ST32.

In step ST32, the processor 7 makes a determination not to change the imaging conditions. In other words, at time t4, the lower extremity vein of the subject S22 is not imaged under imaging conditions for the lower extremity vein, but for the brachial artery, but if the categories identified in step ST33 match, a determination is made to not change the imaging conditions. The reason is described below.

Category 2 includes the brachial vein parameter set B1, brachial artery parameter set B2, lower extremity vein parameter set B3, and lower extremity artery parameter set B4. The imaging sites for these parameter sets, namely the brachial veins, brachial arteries, lower extremity veins, and lower extremity arteries, are anatomically similar sites to each other. In addition, the values of the parameters used in the imaging of the brachial vein, brachial artery, lower extremity vein, and lower extremity artery are often identical or close to each other. Therefore, if the currently set imaging conditions for the brachial artery are not changed to the deduced imaging conditions for the lower extremity vein, and ultrasonic images of the lower extremity vein are acquired without changing the imaging conditions for the brachial artery, the image quality of the ultrasonic images is not expected to be significantly affected. Therefore, if the categories identified in step ST33 match, a determination is made not to change the imaging conditions. A plurality of parameter sets included in one category are parameter sets for a plurality of sites defined as having approximately similar body compositions in the subject. The body composition includes fat, muscle, bone, and blood vessels. Changing parameter sets among a plurality of parameter sets in one category can produce ultrasonic images with mutually acceptable quality.

Therefore, the user 51 continues the examination of the lower extremity vein of the subject S22 under the imaging conditions for the brachial artery after time t4. On the other hand, the processor 7 continues to periodically execute process 42 after time t4. It can be assumed that the process 42 was executed after time t4, but it was determined (step ST32) not to change the imaging conditions. Therefore, the examination of the lower extremity vein of the subject S22 was completed without any automatic changes in the imaging conditions being made. In FIG. 11, the end point of the examination of the lower extremity vein of the subject S22 is indicated at t5. After the examination of the subject S22 is completed, examination of the next new subject S23 is initiated. It can be assumed that the imaging site of the new subject S23 is the thyroid gland.

The user 51 prepares for the examination of the thyroid gland of the subject S23 after completing the examination of the immediately preceding subject S22. In this case, the imaging site is changed from the lower extremity vein to the thyroid gland, so the user 51 must change the imaging conditions from imaging conditions for the brachial artery to the imaging conditions for the thyroid gland. In the following, however, the case is considered in which the user 51 initiates an examination of the thyroid gland of a new subject S23 without changing the imaging conditions.

The user 51 initiates the examination of the thyroid gland of the new subject S23. Here, the time of disclosure of the examination of the thyroid gland of the new subject S23 is indicated to be at t6.

The user 51 initiates a thyroid gland examination of the new subject S23 at time t6, but does not change the imaging conditions, so the set imaging conditions remain the same as the imaging conditions for the brachial artery. Therefore, the user 51 initiates the examination of the thyroid gland of the subject S23 under the imaging conditions for the brachial artery.

On the other hand, the processor 7 periodically executes the process 42 after the examination of the thyroid gland of the subject S23 begins at time t6. The present embodiment describes the case where the process 42 is executed at time t7 after time t6.

When process 42 is initiated, first, in step ST10, the processor 7 identifies the imaging site in the ultrasonic image acquired between time t6 and t7. The identifying step ST10 will be described below.

First, in step ST11, the processor 7 generates an input image 76 for inputting to the trained model 31 by preprocessing the ultrasonic image 75 acquired between time t6 and time t7. The processor 7 generates the input image 76, for example, by preprocessing the ultrasonic image 75 acquired just before time t7. After the input image 76 is generated, the process proceeds to step ST12.

In step ST12, the processor 7 deduces a location indicated by the input image 76 using the trained model 31.
The processor 7 inputs the input image 76 into the trained model 31 and uses the trained model 31 to deduce the sites contained in the input image 76. In the deduction step, the processor 7 calculates the probability that each imaging site is included in the input image 76. Furthermore, the processor 7 then deduces the imaging site in the input image 76 based on the probability calculated for each imaging site.

It can be assumed that the thyroid gland probability exceeds the threshold value. Therefore, the processor 7 deduces that the imaging site included in the input image 76 is the thyroid gland. After deducing the imaging site, the process proceeds to step ST30.

In step ST30, the processor 7 determines whether to change the imaging conditions based on the deduced imaging site. Step ST30 will be described below in detail.

First, in step ST31, the processor 7 determines whether the currently set imaging conditions are those corresponding to the imaging site deduced in step ST12. At time t7, the set imaging condition is the imaging condition for the brachial artery. On the other hand, the imaging site deduced in step ST12 is the thyroid gland. Therefore, at time t7, the set imaging conditions (imaging conditions for the brachial artery) are not the imaging conditions corresponding to the imaging site (thyroid gland) deduced in step ST12, so the process proceeds to step ST33.

Figure 13:
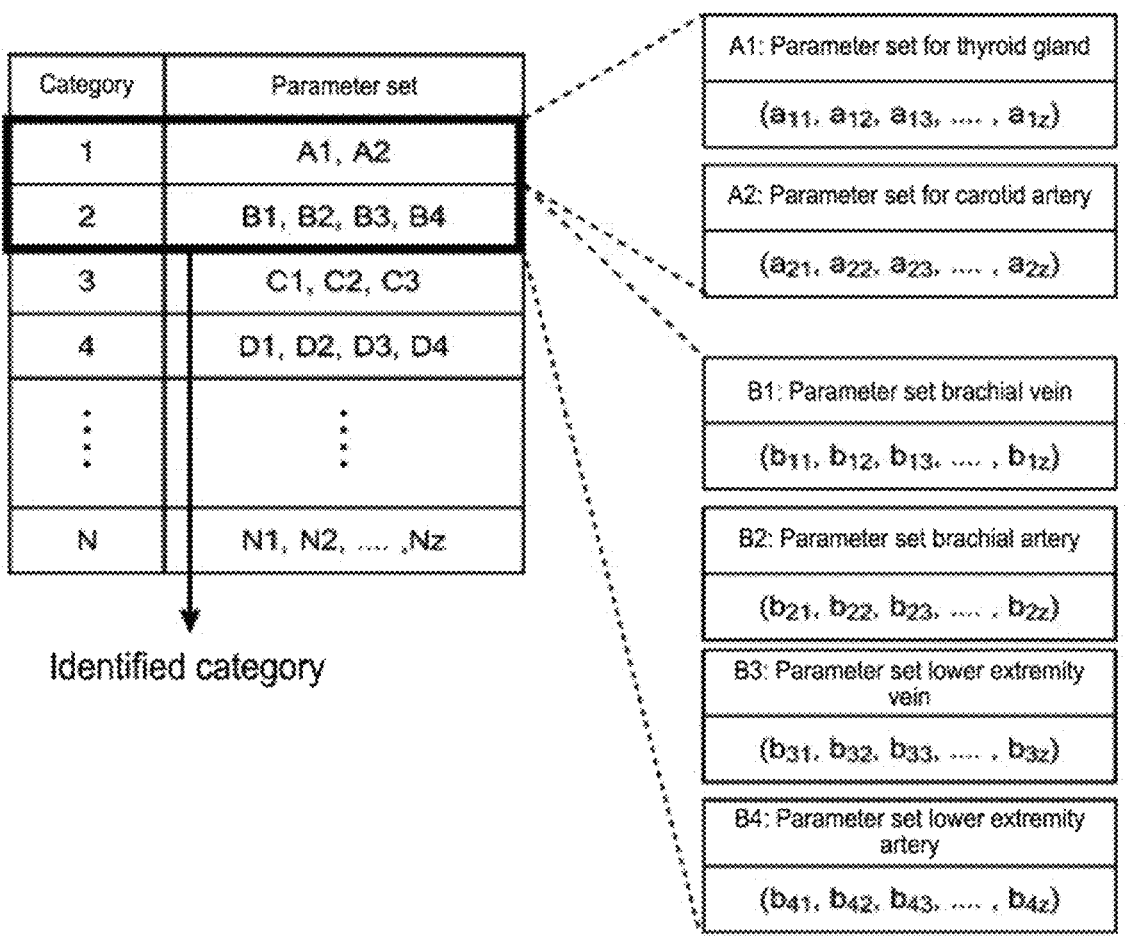
FIG. 13 is an explanatory diagram of step ST33 according to an embodiment.

FIG. 13 is an explanatory diagram of step ST33.

In step ST33, the processor 7 identifies the category corresponding to the deduced imaging site from among the plurality of categories 1 to N registered in the database. Here, the deduced imaging site is the "thyroid gland", so the processor 7 identifies category 1, which includes the parameter set of the thyroid gland, from among the plurality of categories 1 to n.

Next, the processor 7 identifies the category corresponding to the currently set imaging conditions from among the plurality of categories 1 to N registered in the database. Here, the currently set imaging conditions are for the brachial artery, so the processor 7 identifies category 2, which contains the parameter set for the brachial artery, from among the plurality of categories 1 to N. After identifying category 2, the process proceeds to step ST34.

In step ST34, the processor 7 determines whether the two categories identified in step ST33 match. If the categories match, the process proceeds to step ST32, while if the categories do not match, the process proceeds to step ST35. Here, the identified categories do not match (categories 1 and 2), so the process proceeds to step ST35.

In step ST35, the processor 7 makes a determination to change the imaging conditions. In other words, the processor 7 makes a determination to change the imaging conditions if the categories are found not to match. The reason is described below.

Categories 1 and 2 are categorized by the imaging site, which are not anatomically similar. Therefore, the imaging sites belonging to category C1 and the imaging sites belonging to category C2 are imaging sites that are easily distinguished from each other because of the pronounced anatomical differences. In addition, there are often significant differences in the values of the parameters set in the imaging conditions when comparing the imaging sites in Category 1 and the imaging sites in Category 2. Therefore, if the imaging conditions for the brachial artery set at time t7 are changed to the deduced imaging conditions for the thyroid gland and ultrasonic images of the thyroid gland are acquired, it is conceivable that the quality of the acquired ultrasonic images can be greatly improved. Therefore, if the two categories identified in step ST33 match, a determination is made to change the imaging conditions.

If a determination is made to change the imaging conditions, the process proceeds to step ST36, and the processor 7 changes the imaging conditions for the brachial artery set at time t7 to the imaging conditions for the thyroid gland. For example, the processor 7 may change the brachial artery parameter set B1 to the thyroid gland parameter set A1 when changing the imaging conditions. Note that in addition to changing the above parameter set, the processor 7 may also change other conditions not included in the parameter set.

Therefore, the user 51 can perform an examination of the thyroid gland of the subject S23 using the imaging conditions for the thyroid gland immediately after time t7. On the other hand, after time t7, the processor 7 continues to periodically execute the aforementioned process 42. Furthermore, when the acquisition of all images necessary for the examination of the subject S23 is completed, the examination of subject S23 is terminated (at time t8).

In the second embodiment, a plurality of categories 1 to N are registered in the database, as depicted in FIG. 10. Each category contains a plurality of sets of parameters. Each parameter set is classified into one of a plurality of categories 1 to N, based on whether the anatomical features of the imaging site are similar and/or whether the parameter values are similar. For example, the brachial veins, brachial arteries, lower extremity veins, and lower extremity arteries are all blood vessels, so they are anatomically similar and have the same or similar parameter values used in the imaging conditions. Therefore, the brachial vein, brachial artery, lower extremity vein, and lower extremity artery can produce ultrasonic images of consistent quality regardless of which one of the following parameter sets are used: brachial vein parameter set B1, brachial artery parameter set B2, lower extremity vein parameter set B3, and lower extremity artery parameter set B4. Therefore, in the second embodiment, the brachial vein parameter set B1, brachial artery parameter set B2, lower extremity vein parameter set B3, and lower extremity artery parameter set B4 are all classified in the same category 2. Therefore, the imaging conditions are not changed between the brachial vein, brachial artery, lower extremity vein, and lower extremity artery, thus reducing the frequency of automatic changes in imaging conditions at timing unintended by the user 51. Furthermore, parameter sets B1 to B4 have identical or similar parameter values, so ultrasonic images of sufficient quality can also be acquired without any changes in imaging conditions between brachial veins, brachial arteries, lower extremity veins, and lower extremity arteries.

Furthermore, the thyroid gland parameter set A1 and the carotid artery parameter set A2 are classified in the same category 1. Therefore, the imaging conditions are not changed between the thyroid gland and the carotid artery, so the frequency of automatic changes in the imaging conditions at timing unintended by the user 51 can be reduced. Furthermore, parameter sets A1 and A2 have identical or similar parameter values, so ultrasonic images of sufficient quality can be acquired without any changes in imaging conditions between the thyroid gland and the carotid artery.

Furthermore, in the present embodiment, the imaging conditions are changed if the categories identified in step ST33 are different. Here, an example is depicted in which the imaging conditions are changed from W1 for the brachial artery to W2 for the thyroid gland, immediately after time t7. Therefore, if the imaging sites are not anatomically similar or if the differences in the parameter values are large, the currently set imaging conditions can be automatically changed to imaging conditions suitable for the imaging site, thus enabling high-quality ultrasonic images to be acquired.

(3) Embodiment 3

The third embodiment describes an example of imaging a breast. Note that the third embodiment describes an example of performing ultrasonography under imaging conditions according to the size of the breast so that a higher quality breast image can be obtained.

In the third embodiment, the ultrasonic examination is performed under imaging conditions according to the breast size, so a trained model capable of identifying breast size is prepared. This trained model is created as follows.

Figure 14:
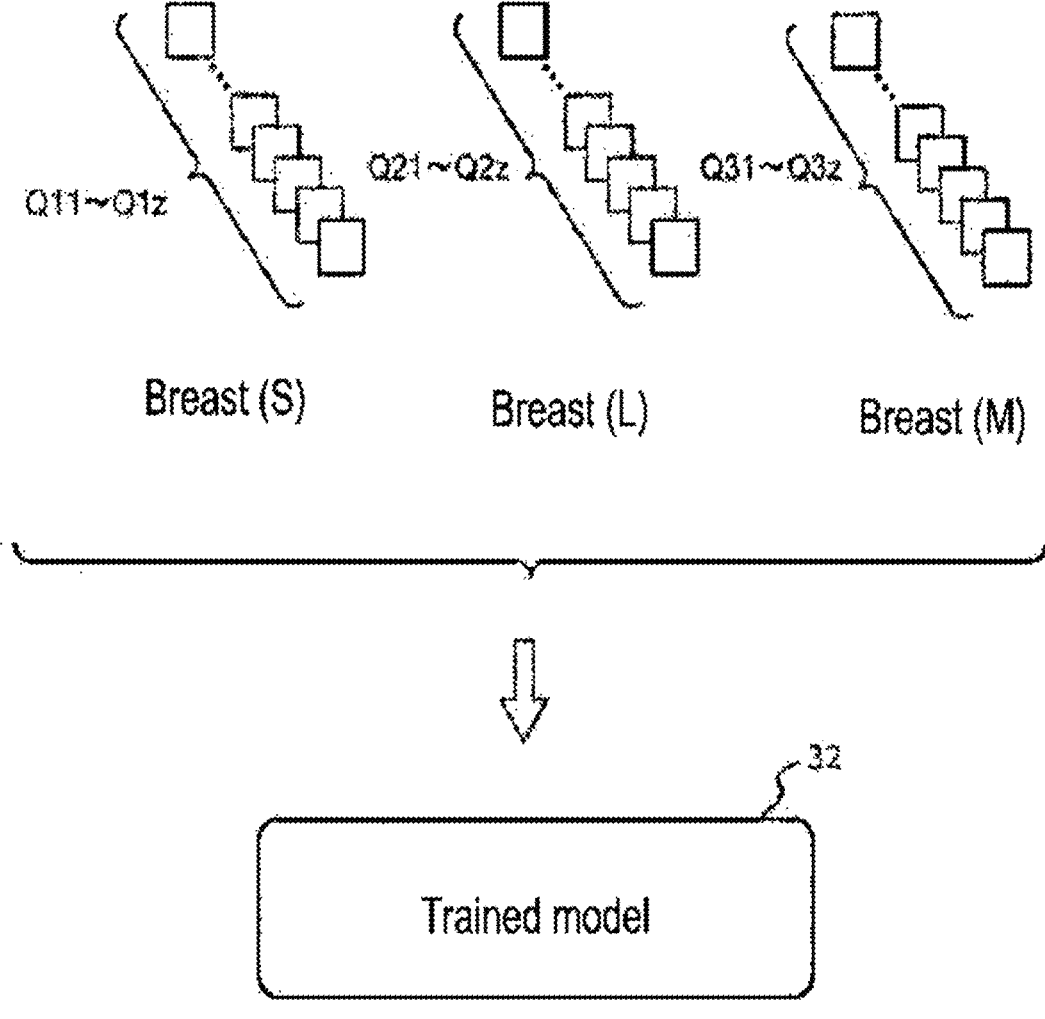
FIG. 14 is an explanatory diagram of the training image used to create the trained model according to an embodiment.

FIG. 14 is an explanatory diagram of the training image used to create the trained model of the third embodiment.

First, training images with different breast sizes are prepared as the training images. Here, three types of training images were prepared as training images with different breast sizes. First are training images Q11 to Q1z of a small size breast (hereinafter referred to as "breast (S)"), second are training images Q21 to Q2z of a standard size breast (hereinafter referred to as "breast (M)"), and third are training images Q 31 to Q3z of a large size breast (hereinafter referred to as "breast (L)").

Furthermore, each training image is labeled with breast (S), breast (M), or breast (L) as the correct data.

Furthermore, the neural network is trained by including training images Q11 to Q1z, Q21 to Q2z, and Q31 to Q3z in the training images used to create the trained model. This creates a trained model that identifies differences in breast size.

Next, a set of parameters is registered in the database according to the size of the breast.

Figure 15:
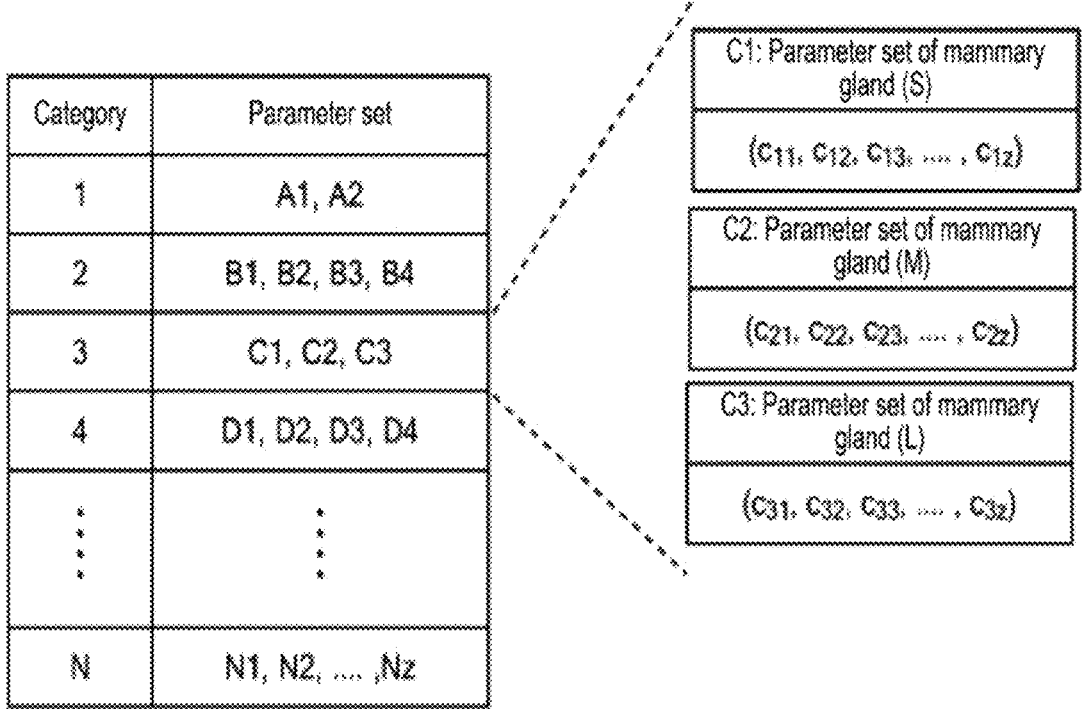
FIG. 15 is an explanatory diagram of the set of parameters corresponding to breast size according to an embodiment.

FIG. 15 is an explanatory diagram of the set of parameters corresponding to breast size.

Category 3 includes breast (S) parameter set C1, breast (M) parameter set C2, and breast (L) parameter set C3. These parameter sets C1 to C3 are registered in the database to be included in category 3.

The breast (S) parameter set C1 contains a plurality of parameters that are used when examining a subject with a small breast size. In FIG. 15, the parameters included in the breast (S) parameter set C1 are indicated by $(c_{11}, c_{12}, c_{13}, \ldots c_{1z})$. These parameters $c_{11}$ to $c_{1z}$ include, for example, frequency and depth.

The breast (M) parameter set C2 contains a plurality of parameters that are used when examining a subject with a standard-sized breast. In FIG. 15, the parameters included in the breast (M) parameter set C2 are indicated by $(c_{21}, c_{22}, c_{23}, \ldots c_{2z})$. These parameters c21 to c2z include, for example, frequency and depth.

The breast (L) parameter set C3 contains a plurality of parameters that are used when examining a subject with a large breast size. In FIG. 15, the parameters included in the breast (L) parameter set C3 are indicated by $(c_{31}, c_{32}, c_{33}, \ldots c_{3z})$. These parameters c31 to c3z include, for example, frequency and depth. Parameter sets C1, C2, and C3 are parameter sets set according to different compositions at one site (here, the breast). "Different compositions" include cases in which the proportions of each component of the body composition or the combination of each component is different. Here, parameter sets C1, C2 and C3 are set according to the amount of fat in the breast, with parameter sets C1, C2 and C3 in order of increasing fat content. Changing parameter sets between parameter sets C1, C2 and C3 can produce ultrasonic images of mutually acceptable quality.

In the third embodiment, the aforementioned trained model 32 and the database are used to examine the subject. The examination flow of the subject is described below.

Figure 16:
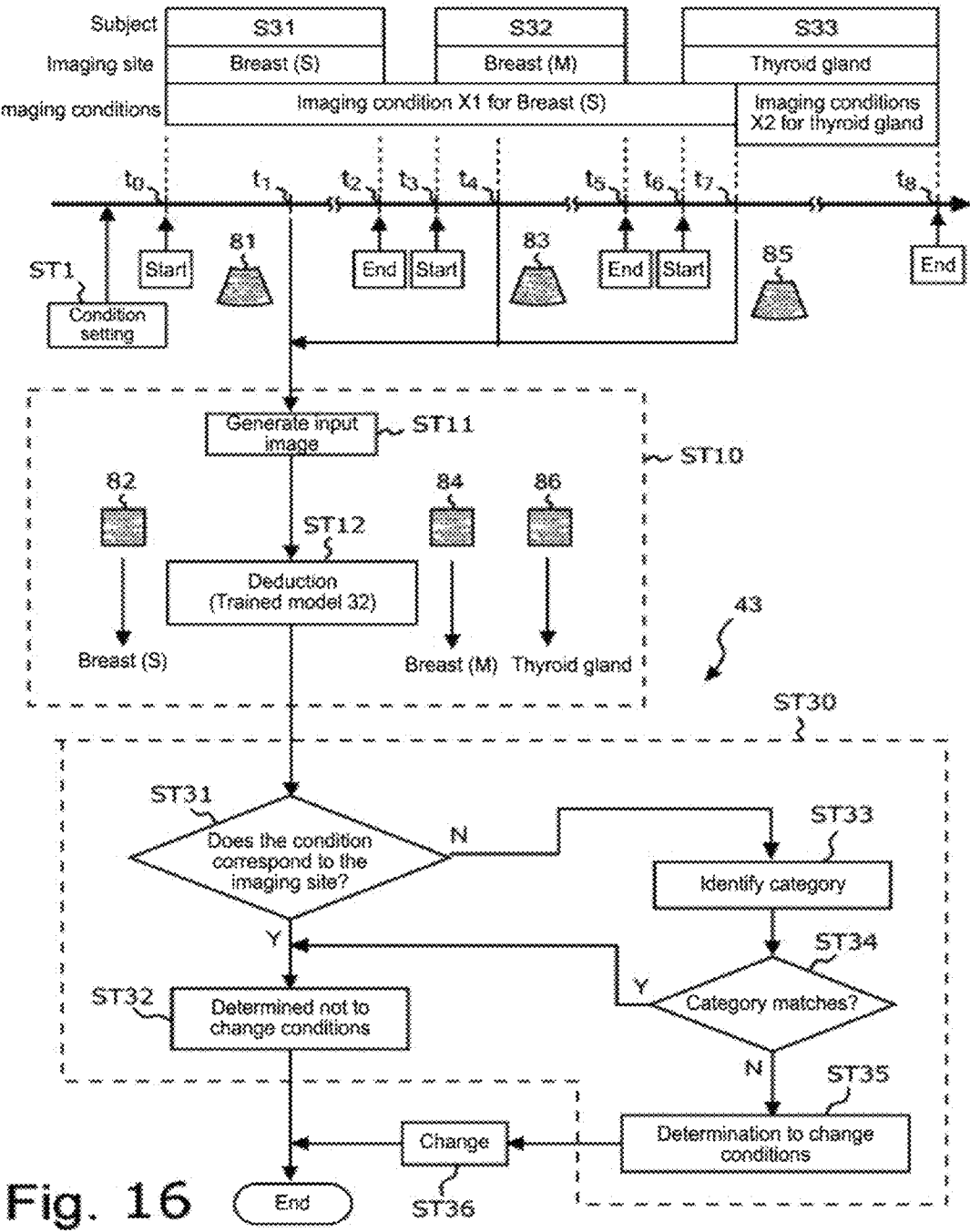
FIG. 16 is a diagram depicting an example of a flowchart executed during an examination of a subject according to an embodiment.

FIG. 16 is a diagram depicting an example of a flowchart executed during an examination of a subject.

In step ST1, the user 51 leads the subject to the examination room and places the subject on the examination bed. The user 51 operates the user interface 10 (see FIG. 2) to enter patient information, set imaging conditions for acquiring ultrasonic images of the subject, and make other necessary settings. Here, it can be assumed that the imaging site of the subject is the breast (S) (small sized breast). Therefore, the user 51 sets the imaging conditions for the breast (S).

When the user 51 is ready for the examination, the user begins examining the subject. In FIG. 16, the inspection start time is indicated as t0.

In FIG. 16, "subject", "imaging site", and "imaging conditions" are depicted on the time axis. The "subject" represents the subject being examined, "imaging site" represents the imaging site of the subject, and "imaging conditions" represents the imaging conditions set for the ultrasonic diagnostic device. For example, at time to when the examination starts, the diagram depicts that the "subject" is subject S31, the "imaging site" is the breast (S), and the "imaging conditions" are the X1 imaging conditions for the breast (S).

The user 51 operates the probe while pressing the ultrasonic probe 2 against the breast of the subject S31 to examine the subject S31. The ultrasonic probe 2 transmits an ultrasonic wave and receives an echo reflected from within the subject S31. The received echo is converted to an electrical signal, and this electrical signal is output as an echo signal to the receiving apparatus 5 (see FIG. 2). The receiver 5 executes a prescribed process on the echo signal and outputs the echo signal to the reception beamformer 6. The reception beamformer 6 executes reception beamforming on the signal received through the receiver 5 and outputs echo data.

The processor 7 generates an ultrasonic image based on the echo data.

The user 51 can review the generated ultrasonic images or save the ultrasonic images if necessary. Furthermore, the user 51 continues to perform the examination of the subject. On the other hand, the processor 7 periodically executes a process 43 after the examination of subject S31 starts at time t0 to determine whether the imaging conditions should be changed and to automatically change the imaging conditions as necessary. In the present embodiment, the first process 43 is executed at time t1 after the inspection start time to. The process 43 is described below.

When process 43 is initiated, first, in step ST10, the processor 7 identifies the imaging site in the ultrasonic image acquired between time t0 and t1. The identifying step ST10 will be described below.

First, in step ST11, the processor 7 generates an input image 82 for inputting to the trained model 32 by preprocessing the ultrasonic image 81 acquired between time to and time t1. The processor 7 generates the input image 82, for example, by preprocessing the ultrasonic image 81 acquired just before time t1. After the input image 82 is generated, the process proceeds to step ST12.

In step ST12, the processor 7 deduces a location indicated by the input image 82 using the trained model 32.
The processor 7 inputs the input image 82 into the trained model 32 and uses the trained model 32 to deduce the sites contained in the input image 82. In the deduction step, the processor 7 calculates the probability that each imaging site is included in the input image 82. Furthermore, the processor 7 then deduces the imaging site in the input image 82 based on the probability calculated for each imaging site.

It can be assumed that the breast (S) probability exceeds the threshold value. Therefore, the processor 7 deduces that the imaging site included in the input image 82 is the breast (S). After deducing the imaging site, the process proceeds to step ST30.

In step ST30, the processor 7 determines whether to change the imaging conditions based on the deduced imaging site. Step ST30 will be described below in detail.

First, in step ST31, the processor 7 determines whether the currently set imaging conditions are those corresponding to the imaging site deduced in step ST12. At time t1, the set imaging condition is the imaging condition for the breast (S). On the other hand, the imaging site deduced in step ST12 is the breast (S). Therefore, the currently set imaging conditions are the imaging conditions corresponding to the imaging site (breast (S)) deduced in step ST12. Therefore, proceeding to step ST32, the processor 7 makes a determination not to change the imaging conditions, and terminates the process 43.

On the other hand, the user 51 continues the examination of the subject S31 while operating the ultrasonic probe 2 after time t1. After time t1, the processor 7 periodically executes the aforementioned process 43. It can be assumed that the imaging of the breast (S) of the subject S31 is completed without any change in imaging conditions. The end of the examination of the breast (S) of the subject S31 is indicated by "t2".

After the examination of the subject S31 is completed, the next new subject S32 is prepared for examination. Note that in this case, it is assumed that the new subject S32 is a breast, but the breast is a standard size. Therefore, in this case, the imaging site is changed from a small size breast ("Breast (S)") to a standard size breast ("Breast (M)"), and the user 51 must change the imaging conditions from the imaging conditions for Breast (S) to the imaging conditions for Breast (M). In the following, however, the case is considered in which the user 51 initiates an examination of the breast (M) of a new subject S32 without changing the imaging conditions.

The user 51 initiates the examination of the breast (M) of the new subject S32. Here, the time of disclosure of the examination of the breast (M) of the new subject S32 is indicated to be at t3.

The user 51 starts examining the breast (M) of the subject S32 at time t3, but since the imaging conditions have not been changed, the set imaging conditions remain the same as the imaging conditions for the breast (S). Therefore, the user 51 starts the examination of the breast (M) of the subject S32 under the imaging conditions for breast (S).

On the other hand, the processor 7 periodically executes the process 43 after the examination of the breast (M) of the subject S32 begins at time t3. The present embodiment describes the case where the process 43 is executed at time t4 after time t3.

First, in step ST11, the processor 7 generates an input image 84 for inputting to the trained model 32 by preprocessing the ultrasonic image 83 acquired between time t3 and time t4. The processor 7 generates the input image 84, for example, by preprocessing the ultrasonic image 83 acquired just before time t4. After the input image 84 is generated, the process proceeds to step ST12.

In step ST12, the processor 7 deduces a location indicated by the input image 84 using the trained model 32. In the deduction step, the processor 7 calculates the probability that each imaging site is included in the input image 84. Furthermore, the processor 7 then deduces the imaging site in the input image 84 based on the probability calculated for each imaging site.

It can be assumed that the breast (M) (standard size breast) probability exceeds the threshold value. Therefore, the processor 7 deduces that the imaging site included in the input image 84 is the breast (M). After deducing the imaging site, the process proceeds to step ST30.

In step ST30, the processor 7 determines whether to change the conditions based on the deduced imaging site. Step ST30 will be described below in detail.

First, in step ST31, the processor 7 determines whether the currently set imaging conditions are those corresponding to the imaging site deduced in step ST12. At time t4, the set imaging condition is the imaging condition for the breast (S). On the other hand, the imaging site deduced in step ST12 is the breast (M). Therefore, at time t4, the set imaging conditions (imaging conditions for the breast (M)) are not the imaging conditions corresponding to the imaging site (breast (S)) deduced in step ST12, so the process proceeds to step ST33.

Figure 17:
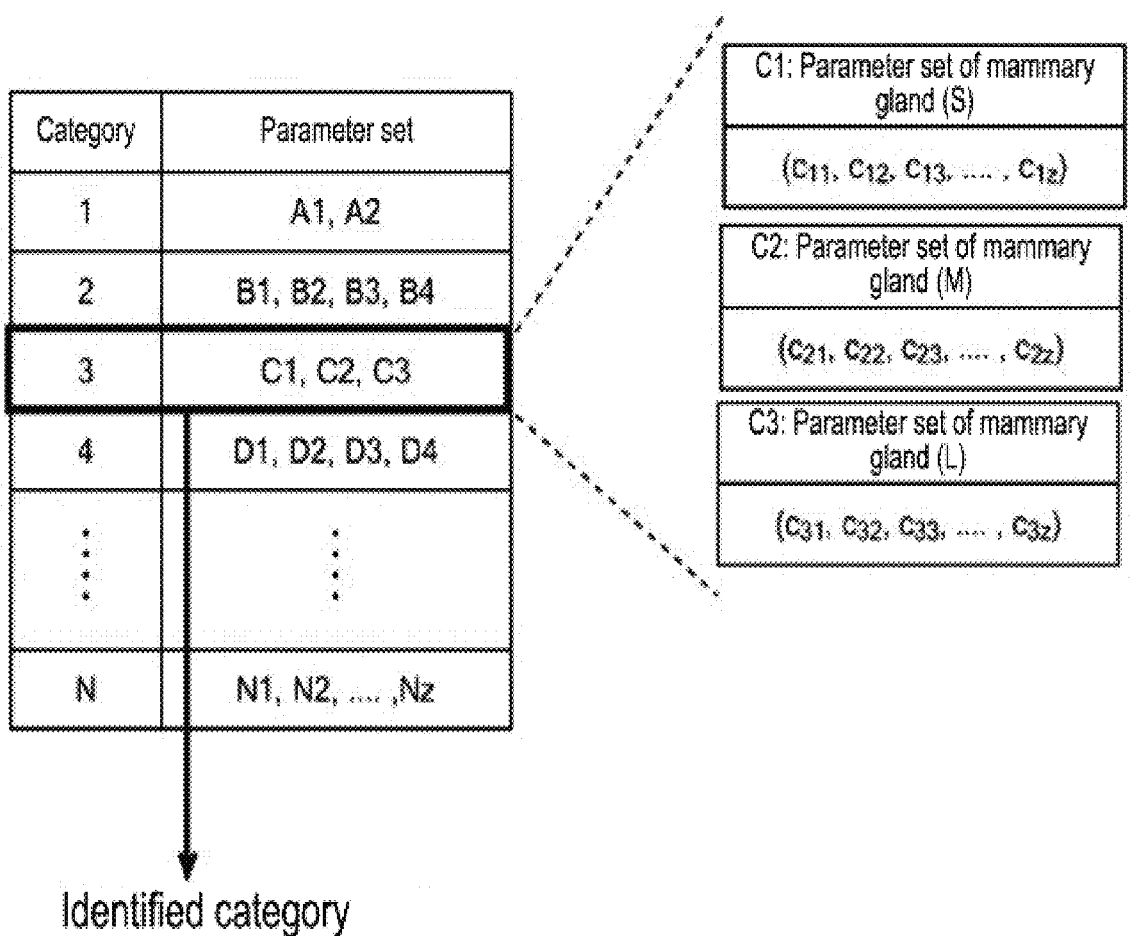
FIG. 17 is an explanatory diagram of step ST33 according to an embodiment.

FIG. 17 is an explanatory diagram of step ST33.

In step ST33, the processor 7 identifies the category corresponding to the deduced imaging site from among the plurality of categories 1 to N registered in the database. Here, the deduced imaging site is the "breast (M)", so the processor 7 identifies category 3, which includes the parameter set of the breast (M), from among the plurality of categories 1 to n.

Next, the processor 7 identifies the category corresponding to the currently set imaging conditions from among the plurality of categories 1 to N registered in the database. Here, the currently set imaging conditions are for the breast (M), so the processor 7 identifies category 3, which contains the parameter set for the breast (M), from among the plurality of categories 1 to N. After identifying category 3, the process proceeds to step ST34.

In step ST34, the processor 7 determines whether the two categories identified in step ST33 match. If the categories match, the process proceeds to step ST32, while if the categories do not match, the process proceeds to step ST35. Here, the identified categories match (category 3), so the process proceeds to step ST32.

In step ST32, the processor 7 makes a determination not to change the imaging conditions. In other words, at time t4, the breast (M) of the subject S32 is not imaged under imaging conditions for the breast (M), but for the breast (S), but if the categories identified in step ST33 match, a determination is made to not change the imaging conditions. The reason is described below.

As described above, parameter sets C1, C2, and C3 are set according to the size of the breast, but the organ to be imaged is the "breast" in all cases. Therefore, it is possible to obtain ultrasonic images of sufficient quality even if the breast (M) is imaged using the parameter set of the breast (S) or the breast (L). Therefore, in the present embodiment, a determination is made not to change the imaging conditions.

Therefore, the user 51 continues the examination of the breast (M) of the subject S32 under the imaging conditions for breast (S) from time t4 and later. On the other hand, the processor 7 periodically executes the above process 43 during the examination of the subject S32. It can be assumed that the process 43 was executed after time t4, but it was determined (step ST32) not to change the imaging conditions. Therefore, the examination of the breast (M) of the subject S32 was completed without any automatic changes in the imaging conditions being made. In FIG. 16, the end point of the examination of the breast (M) of the subject S32 is indicated at t5. After the examination of the subject S32 is completed, examination of the next new subject S33 is initiated. It can be assumed that the imaging site of the new subject S33 is the thyroid gland.

The user 51 prepares for the examination of the thyroid gland of the new subject S33 after completing the examination of the immediately preceding subject S32. In this case, the imaging site is changed from the breast to the thyroid gland, so the user 51 must change the imaging conditions from imaging conditions for the breast (S) to the imaging conditions for the thyroid gland. In the following, however, the case is considered in which the user 51 initiates an examination of the thyroid gland of a new subject S33 without changing the imaging conditions.

The user 51 initiates the examination of the thyroid gland of the new subject S33. Here, the time of disclosure of the examination of the thyroid gland of the new subject S33 is indicated to be at t6.

The user 51 initiates a thyroid gland examination of the new subject S33 at time t6, but does not change the imaging conditions, so the set imaging conditions remain the same as the imaging conditions X1 for the breast (S). Therefore, the user 51 starts the examination of the thyroid gland of the subject S33 under the imaging conditions X1 for breast (S).

On the other hand, the processor 7 periodically executes the process 43 after the examination of the thyroid gland of the subject S33 begins at time t6. The present embodiment describes the case where the process 43 is executed at time t7 after time t6.

When process 43 is initiated, first, in step ST10, the processor 7 identifies the imaging site in the ultrasonic image acquired between time t6 and t7. The identifying step ST10 will be described below.

First, in step ST11, the processor 7 generates an input image 86 for inputting to the trained model 32 by preprocessing the ultrasonic image 85 acquired between time t6 and time t7. The processor 7 generates the input image 86, for example, by preprocessing the ultrasonic image 85 acquired just before time t7. After the input image 86 is generated, the process proceeds to step ST12.

In step ST12, the processor 7 deduces a location indicated by the input image 86 using the trained model 32.
The processor 7 inputs the input image 86 into the trained model 32 and uses the trained model 32 to deduce the sites contained in the input image 86. In the deduction step, the processor 7 calculates the probability that each imaging site is included in the input image 86. Furthermore, the processor 7 then deduces the imaging site in the input image 86 based on the probability calculated for each imaging site.

It can be assumed that the thyroid gland probability exceeds the threshold value. Therefore, the processor 7 deduces that the imaging site included in the input image 86 is the thyroid gland. After deducing the imaging site, the process proceeds to step ST30.

In step ST30, the processor 7 determines whether to change the imaging conditions based on the deduced imaging site. Step ST30 will be described below in detail.

First, in step ST31, the processor 7 determines whether the currently set imaging conditions are those corresponding to the imaging site deduced in step ST12. At time t7, the set imaging condition is the imaging condition for the breast (S). On the other hand, the imaging site deduced in step ST12 is the thyroid gland. Therefore, at time t7, the set imaging conditions (imaging conditions for the thyroid gland) are not the imaging conditions corresponding to the imaging site (breast (S)) deduced in step ST12, so the process proceeds to step ST33.

Figure 18:
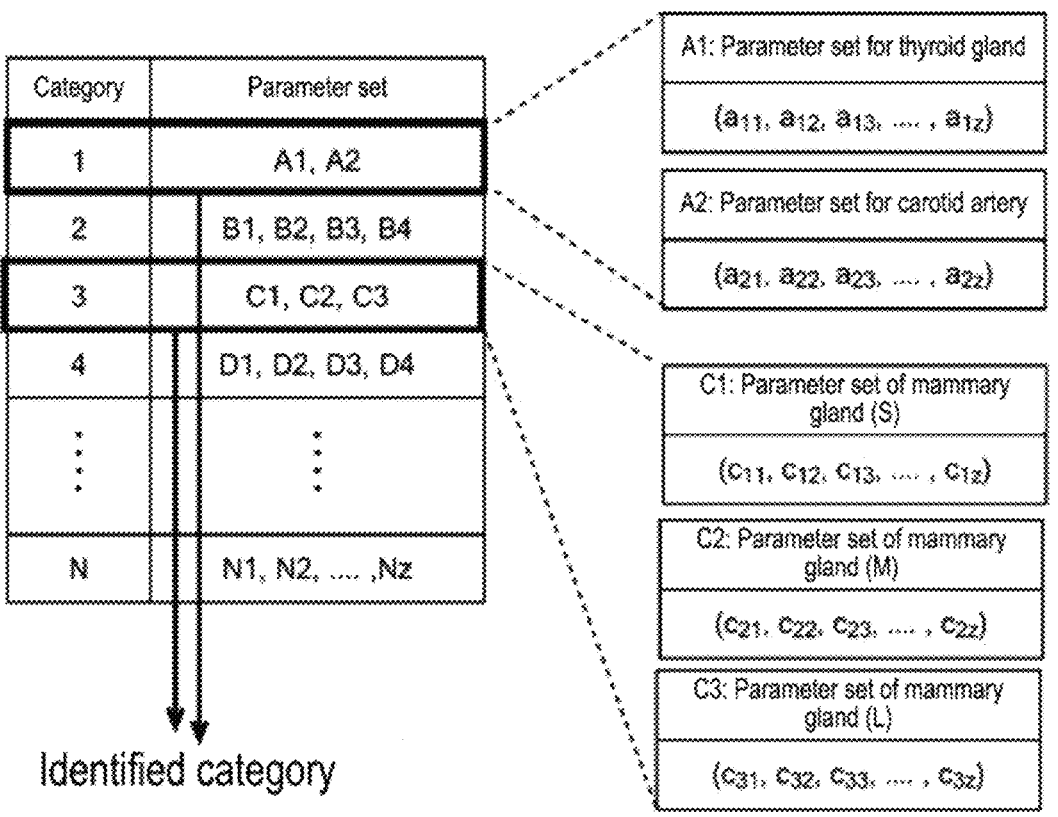
FIG. 18 is an explanatory diagram of step ST33 according to an embodiment.

FIG. 18 is an explanatory diagram of step ST33.
In step ST33, the processor 7 identifies the category corresponding to the deduced imaging site from among the plurality of categories 1 to N registered in the database. Here, the deduced imaging site is the "thyroid gland", so the processor 7 identifies category 1, which includes the parameter set of the thyroid gland, from among the plurality of categories 1 to N.

Next, the processor 7 identifies the category corresponding to the currently set imaging conditions from among the plurality of categories 1 to N in the database. Here, the currently set imaging conditions are for the breast (M), so the processor 7 identifies category 3, which contains the parameter set for the breast (M), from among the plurality of categories 1 to N. After identifying category 3, the process proceeds to step ST34.

In step ST34, the processor 7 determines whether the two categories identified in step ST33 match. If the categories match, the process proceeds to step ST32, while if the categories do not match, the process proceeds to step ST35. Here, the identified categories do not match (categories 1 and 3), so the process proceeds to step ST35.

In step ST35, the processor 7 makes a determination to change the imaging conditions. In other words, the processor 7 makes a determination to change the imaging conditions if the categories are found not to match. The reason is described below.

Categories 1 and 3 are categorized by the site of imaging, which is not anatomically similar. Therefore, the imaging sites belonging to category 1 and the imaging sites belonging to category 3 are imaging sites that are easily distinguished from each other because of the pronounced anatomical differences. In addition, there are often significant differences in the values of the parameters set in the imaging conditions when comparing the imaging sites in Category 1 and the imaging sites in Category 3. Therefore, it is thought that if the currently set imaging conditions for the breast (S) are changed to the deduced thyroid gland imaging conditions, the quality of the acquired ultrasonic images can be greatly improved. Therefore, if the two categories identified in step ST33 match, a determination is made to change the imaging conditions.

If a determination is made to change the imaging conditions, the process proceeds to step ST36, and the processor 7 changes the imaging conditions for the breast (S) set at time t7 to the imaging conditions for the thyroid gland. For example, the processor 7 may change the breast (S) parameter set C1 to the thyroid gland parameter set A1 when changing the imaging conditions. Note that in addition to changing the above parameter set, the processor 7 may also change other conditions not included in the parameter set.

Therefore, the user 51 can perform an examination of the thyroid gland of the subject S33 using the imaging conditions X2 for the thyroid gland immediately after time t7. On the other hand, after time t7, the processor 7 continues to periodically execute the aforementioned process 43. Furthermore, when the acquisition of all images necessary for the examination of the subject S33 is completed, the examination of subject S33 is terminated (at time t8).

In the third embodiment, category 3 of the database includes breast (S) parameter set C1, breast (M) parameter set C2, and breast (L) parameter set C3. Breast (S), breast (M), and breast (L) all have a breast in common as the organ; furthermore, the values of the parameters used in the imaging conditions are identical or similar. Thus, breast (S), breast (M), and breast (L) can provide ultrasonic images of constant quality regardless of which of the parameter sets C1, C2, and C3 are used. Therefore, in the third embodiment, breast (S) parameter set C1, breast (M) parameter set C2, and breast (L) parameter set C3 are all classified in the same category 3. By classifying the parameter sets C1, C2, and C3 into the same category 3, it is possible to prevent changes in imaging conditions between breast (S), breast (M), and breast (L), thus reducing the frequency of automatic changes in imaging conditions at timing unintended by the user 51. In addition, since the breast (S) parameter set C1, breast (M) parameter set C2, and breast (L) parameter set C3 have the same or similar parameter values, ultrasonic images of sufficient quality can be acquired without any changes in imaging conditions between breast (S), breast (M), and breast (L).

(4) Embodiment 4

The fourth embodiment describes an example in which imaging conditions for the liver, kidneys, and intestines are classified in the same category. In order to provide a more useful diagnosis for each patient, an example is described in which the imaging conditions for a healthy liver and those for a diseased liver are set separately. Therefore, in the fourth embodiment, a trained model is provided that can discriminate between healthy livers and livers with lesions. The following describes the method whereby this trained model is created.

Figure 19:
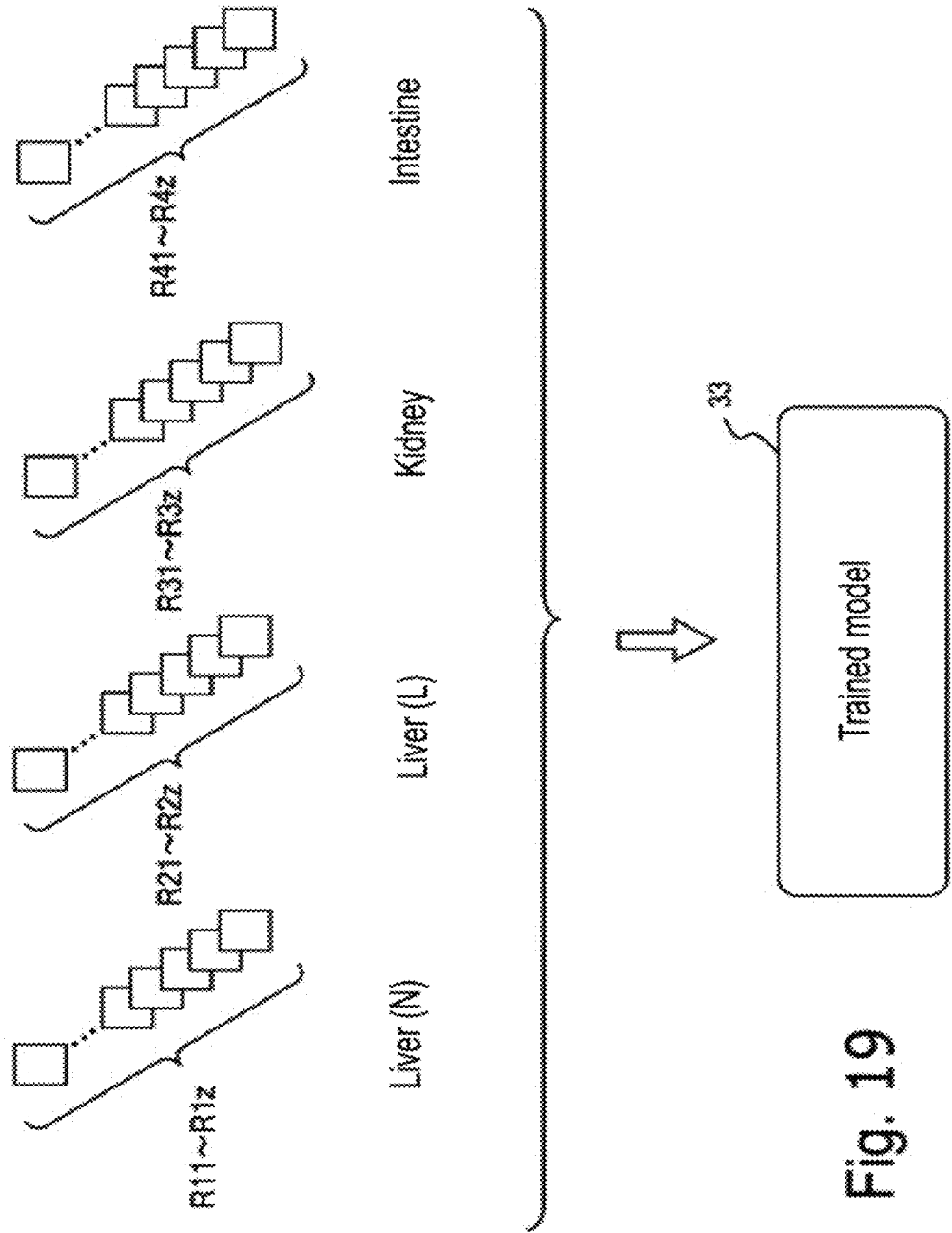
FIG. 19 is an explanatory diagram of the training image used to create the trained model according to an embodiment.

FIG. 19 is an explanatory diagram of the training image used to create the trained model of the fourth embodiment. First, training images are prepared, such as training images R11 to R1z of a healthy liver (hereinafter referred to as "liver (N)") and R21 to R2z of a liver with lesions (hereinafter referred to as "liver (L)").

In addition, training images R31 to R3z for the kidneys and R41 to R4z for the intestines are prepared as training images. Each training image is then labeled with liver (N), liver (L), kidney, and intestine as the correct data.

Next, the neural network is trained by including training images R11 to R1z, R21 to R2z, R31 to R3z, and R41 to R4z in the training images used to create the trained model. This allows for the creation of trained models that identify healthy livers, diseased livers, kidneys, and intestines.

Next, a healthy liver parameter set, a diseased liver parameter set, a kidney parameter set, and an intestine parameter set are registered in the database.

Figure 20:
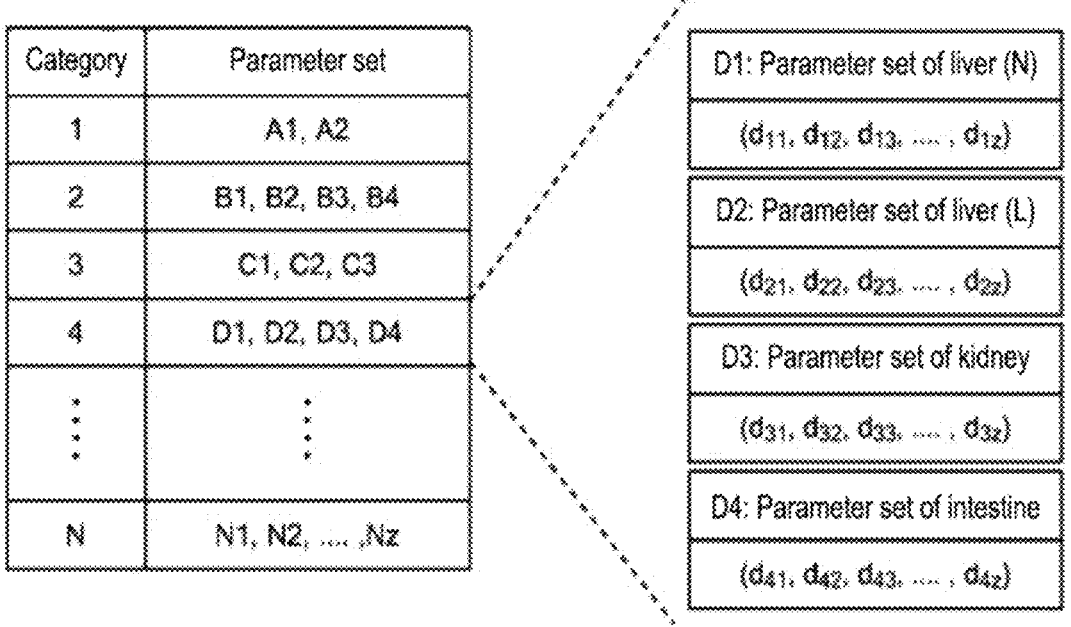
FIG. 20 is an explanatory diagram of the parameter set to be registered according to an embodiment.

FIG. 20 is an explanatory diagram of the parameter set to be registered.

Category 4 includes liver (N) parameter set D1, liver (L) parameter set D2, kidney parameter set D3, and intestine parameter set D4. These parameter sets D1 to D4 are registered in the database to be included in category 4.

The liver (N) parameter set D1 contains a plurality of parameters that are used when examining a healthy liver. In FIG. 20, the parameters included in the liver (N) parameter set D1 are indicated by ($d_{11}$, $d_{12}$, $d_{13}$, . . . $d_{1z}$). These parameters $d_{11}$ to $d_{1z}$ include, for example, frequency and depth.

The liver (L) parameter set D2 contains a plurality of parameters that are used when examining a liver containing lesions. In FIG. 20, the parameters included in the liver (L) parameter set D2 are indicated by ($d_{21}$, $d_{22}$, $d_{23}$, . . . $d_{2z}$). These parameters $d_{21}$ to $d_{2z}$ include, for example, frequency and depth.

The kidney parameter set D3 contains a plurality of parameters that are used when examining the kidneys. In FIG. 20, the parameters included in the liver (N) parameter set D3 are indicated by ($d_{31}$, $d_{32}$, $d_{33}$, . . . $d_{3z}$). These parameters $d_{31}$ to $d_{3z}$ include, for example, frequency and depth.

The intestine parameter set D4 includes a plurality of parameters that are used when examining the intestine. In FIG. 20, the parameters included in the intestine parameter set D4 are indicated by ($d_{41}$, $d_{42}$, $d_{43}$, . . . $d_{4z}$). These parameters $d_{41}$ to $d_{4z}$ include, for example, frequency and depth.

In the fourth embodiment, the aforementioned trained model and the database are used to examine the subject. The examination flow of the subject is described below.

Figure 21:
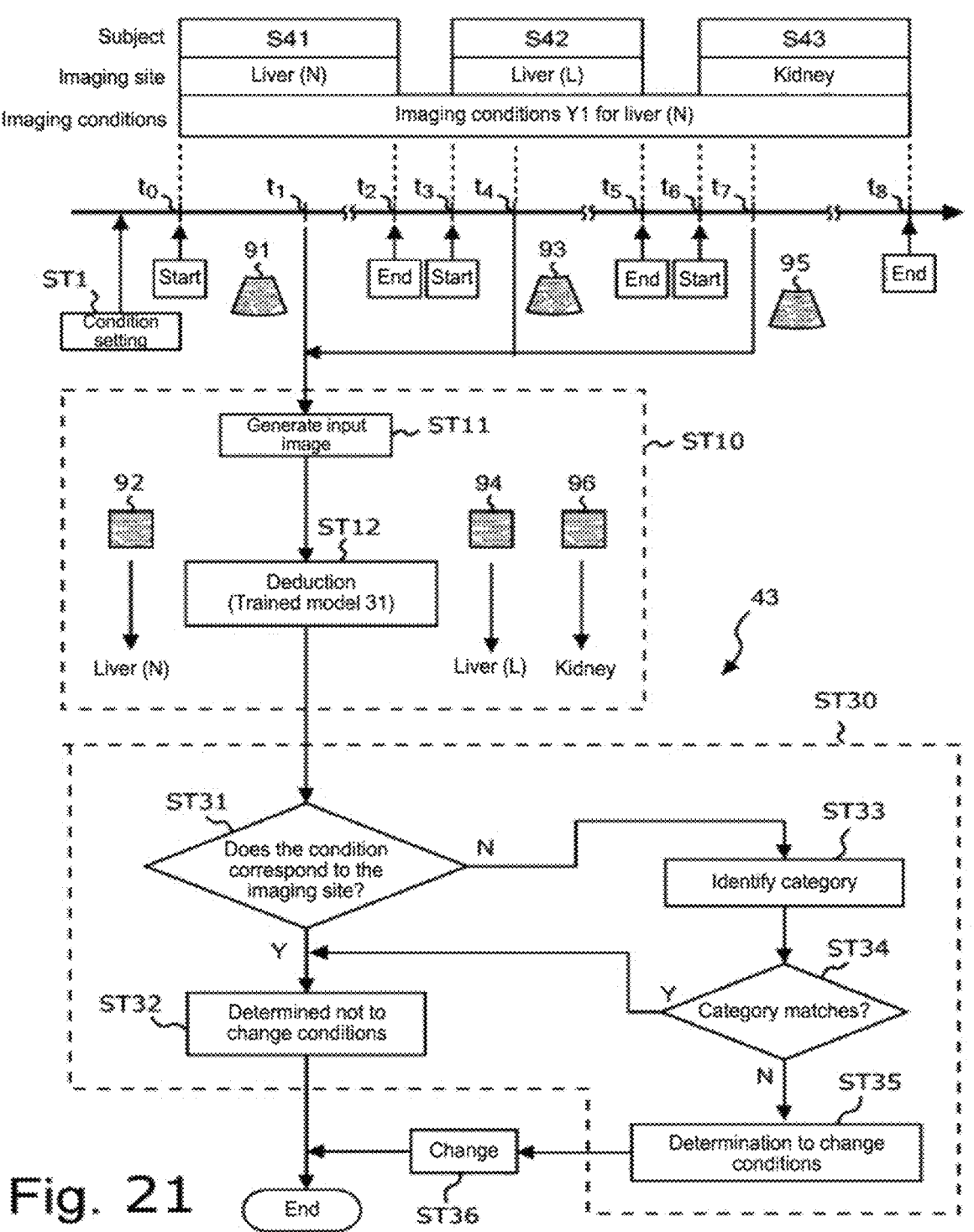
FIG. 21 is a diagram depicting an example of a flowchart executed during an examination of a subject according to an embodiment.

FIG. 21 is a diagram depicting an example of a flowchart executed during an examination of a subject.

In step ST1, the user 51 leads the subject to the examination room and places the subject on the examination bed. The user 51 operates the user interface 10 (see FIG. 2) to enter patient information, set imaging conditions for acquiring ultrasonic images of the subject S33, and make other necessary settings. Here, the imaging site of the subject is set to the "liver (N)". Therefore, the user 51 sets the imaging conditions for the liver (N).

When the user 51 is ready for the examination, the user begins examining the subject. In FIG. 21, the inspection start time is indicated as t0.

Note that in FIG. 21, "subject", "imaging site", and "imaging conditions" are depicted on the time axis. The "subject" represents the subject being examined, "imaging site" represents the imaging site of the subject, and "imaging conditions" represents the imaging conditions set for the ultrasonic diagnostic device. For example, at time to when the examination starts, the diagram depicts that the "subject" is subject S41, the "imaging site" is the liver (N), and the "imaging conditions" are the Y1 imaging conditions for the liver (N).

The user 51 operates the probe while pressing the ultrasonic probe 2 against the liver of the subject S41 to examine the subject S41. The ultrasonic probe 2 transmits an ultrasonic wave and receives an echo reflected from within the subject S41. The received echo is converted to an electrical signal, and this electrical signal is output as an echo signal to the receiving apparatus 5 (see FIG. 2). The receiver 5 executes a prescribed process on the echo signal and outputs the echo signal to the reception beamformer 6. The reception beamformer 6 executes reception beamforming on the signal received through the receiver 5 and outputs echo data. The processor 7 generates an ultrasonic image based on the echo data.

The user 51 can review the generated ultrasonic images or save the ultrasonic images if necessary. Furthermore, the user 51 continues to perform the examination of the subject.

On the other hand, the processor 7 periodically executes a process 44 after the examination of subject S41 starts at time t0 to determine whether the imaging conditions should be changed and to automatically change the imaging conditions as necessary. In the present embodiment, the first process 44 is executed at time t1 after the inspection start time to. The process 44 is described below.

When process 44 is initiated, first, in step ST10, the processor 7 identifies the imaging site in the ultrasonic image acquired between time to and t1. The identifying step ST10 will be described below.

First, in step ST11, the processor 7 generates an input image 82 for inputting to the trained model 33 by preprocessing the ultrasonic image 91 acquired between time t0 and time t1. The processor 7 generates the input image 92, for example, by preprocessing the ultrasonic image 91 acquired just before time t1. After the input image 92 is generated, the process proceeds to step ST12.

In step ST12, the processor 7 deduces a location indicated by the input image 92 using the trained model 33. The processor 7 inputs the input image 92 into the trained model 33 and uses the trained model 33 to deduce the sites contained in the input image 92. In the deduction step, the processor 7 calculates the probability that each imaging site is included in the input image 92. Furthermore, the processor 7 then deduces the imaging site in the input image 92 based on the probability calculated for each imaging site.

It can be assumed that the liver (N) probability exceeds the threshold value. Therefore, the processor 7 deduces that the imaging site included in the input image 92 is the liver (N). After deducing the imaging site, the process proceeds to step ST30.

In step ST30, the processor 7 determines whether to change the imaging conditions based on the deduced imaging site. Step ST30 will be described below in detail.

First, in step ST31, the processor 7 determines whether the currently set imaging conditions are those corresponding to the imaging site deduced in step ST12. At time t1, the set imaging condition is the imaging condition for the liver (N). On the other hand, the imaging site deduced in step ST12 is the liver (N). Therefore, the currently set imaging conditions are the imaging conditions corresponding to the imaging site (liver (N)) deduced in step ST12. Therefore, proceeding to step ST32, the processor 7 makes a determination not to change the imaging conditions, and terminates the process 44.

On the other hand, the user 51 continues the examination of the subject S41 while operating the ultrasonic probe 2 after time t1. After time t1, the processor 7 periodically executes the aforementioned process 44. It can be assumed that the imaging of the liver (N) of the subject S41 is completed without any change in imaging conditions. The end of the examination of the liver (N) of the subject S41 is indicated by "t2".

After the examination of the subject S41 is completed, the next new subject S42 is prepared for examination. Note that, herein, it can be assumed that the new subject S42 to be examined is a liver with lesions. Therefore, in this case, the imaging site is changed from a healthy liver ("liver (N)") to a diseased liver ("liver (L)"), and the user 51 must change the imaging conditions from the imaging conditions Y1 for liver (N) to the imaging conditions for liver (L). In the following, however, the case is considered in which the user 51 initiates an examination of the liver (L) of a new subject S42 without changing the imaging conditions.

The user 51 initiates the examination of the liver (L) of the new subject S42. Here, the time of disclosure of the examination of the liver (L) of the new subject S42 is indicated to be at t3.

The user 51 starts examining the liver (L) of the subject S42 at time t3, but since the imaging conditions have not been changed, the set imaging conditions remain the same as the imaging conditions for the liver (N). Therefore, the user 51 starts the examination of the liver (L) of the subject S42 under the imaging conditions for liver (N).

On the other hand, the processor 7 periodically executes the process 44 after the examination of the liver (L) of the subject S42 begins at time t3. The present embodiment describes the case where the process 44 is executed at time t4 after time t3.

First, in step ST11, the processor 7 generates an input image 94 for inputting to the trained model 33 by preprocessing the ultrasonic image 93 acquired between time t3 and time t4. The processor 7 generates the input image 94, for example, by preprocessing the ultrasonic image 93 acquired just before time t4. After the input image 94 is generated, the process proceeds to step ST12.

In step ST12, the processor 7 deduces a location indicated by the input image 94 using the trained model 33. In the deduction step, the processor 7 calculates the probability that each imaging site is included in the input image 94. Furthermore, the processor 7 then deduces the imaging site in the input image 94 based on the probability calculated for each imaging site.

It can be assumed that the liver (L) (liver with lesions) probability exceeds the threshold value. Therefore, the processor 7 deduces that the imaging site included in the input image 94 is the liver (L). After deducing the imaging site, the process proceeds to step ST30.

In step ST30, the processor 7 determines whether to change the conditions based on the deduced imaging site. Step ST30 will be described below in detail.

First, in step ST31, the processor 7 determines whether the currently set imaging conditions are those corresponding to the imaging site deduced in step ST12. At time t4, the set imaging condition is the imaging condition for the liver (N). On the other hand, the imaging site deduced in step ST12 is the liver (L). Therefore, at time t4, the set imaging conditions (imaging conditions for the liver (L)) are not the imaging conditions corresponding to the imaging site (liver (N)) deduced in step ST12, so the process proceeds to step ST33.

Figure 22:
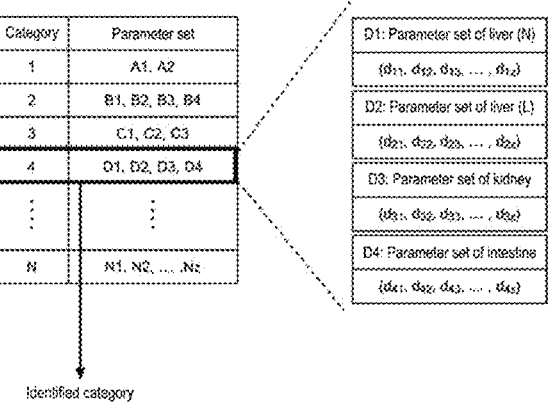
FIG. 22 is an explanatory diagram of step ST33 according to an embodiment.

FIG. 22 is an explanatory diagram of step ST33.

In step ST33, the processor 7 identifies the category corresponding to the deduced imaging site from among the plurality of categories 1 to N registered in the database. Here, the deduced imaging site is the "liver (L)", so the processor 7 identifies category 4, which includes the parameter set of the liver (L), from among the plurality of categories 1 to n.

Next, the processor 7 identifies the category corresponding to the currently set imaging conditions from among the plurality of categories 1 to N registered in the database. Here, the currently set imaging conditions are for the liver (N), so the processor 7 identifies category 4, which contains the parameter set for the liver (N), from among the plurality of categories 1 to n. After identifying category 4, the process proceeds to step ST34.

In step ST34, the processor 7 determines whether the two categories identified in step ST33 match. If the categories match, the process proceeds to step ST32, while if the categories do not match, the process proceeds to step ST35. Here, the identified categories match (category 4), so process proceeds to step ST32.

In step ST32, the processor 7 makes a determination not to change the imaging conditions. In other words, at time t4, the liver (L) of the subject S42 is not imaged under imaging conditions for the liver (L), but for the liver (N), but if the categories identified in step ST33 match, a determination is made to not change the imaging conditions. The reason is described below.

As described earlier, liver (N) and liver (L) share the "liver" as the organ to be imaged. Therefore, it is possible to obtain adequate quality ultrasonic images of the liver (L) even if the liver (N) parameter set is used for imaging. Therefore, in the present embodiment, a determination is made not to change the imaging conditions.

Therefore, the user 51 continues the examination of the liver (L) of the subject S42 under the imaging conditions for liver (N) from time t4 and later. On the other hand, after time t4, the processor 7 continues to periodically execute the aforementioned process 44. It can be assumed that the process 44 was executed after time t4, but it was determined (step ST32) not to change the imaging conditions. Therefore, the examination of the liver (L) of the subject S42 was completed without any automatic changes in the imaging conditions being made. In FIG. 21, the end point of the examination of the liver (L) of the subject S42 is indicated at t5. After the examination of the subject S42 is completed, examination of the next new subject S43 is initiated. It can be assumed that the imaging site of the new subject S43 is the kidney.

The user 51 prepares for the examination of the kidney of the new subject S43 after completing the examination of the immediately preceding subject S42. In this case, the imaging site is changed from the liver to the kidney, so the user 51 must change the imaging conditions from imaging conditions for the liver (N) to the imaging conditions Y1 for the kidney. In the following, however, the case is considered in which the user 51 initiates an examination of the kidney of a new subject S43 without changing the imaging conditions.

The user 51 initiates the examination of the kidney of the new subject S43. Here, the time of disclosure of the examination of the kidney of the new subject S43 is indicated to be at t6.

The user 51 initiates a kidney examination of the new subject S43 at time t6, but does not change the imaging conditions, so the set imaging conditions remain the same as the imaging conditions X1 for the liver (N). Therefore, the user 51 starts the examination of the liver (L) of the subject S43 under the imaging conditions Y1 for the kidney.

On the other hand, the processor 7 periodically executes the process 44 after the examination of the kidney of the subject S43 begins at time t6. The present embodiment describes the case where the process 44 is executed at time t7 after time t6.

When process 44 is initiated, first, in step ST10, the processor 7 identifies the imaging site in the ultrasonic image acquired between time t6 and t7. The identifying step ST10 will be described below.

First, in step ST11, the processor 7 generates an input image 96 for inputting to the trained model 33 by preprocessing the ultrasonic image 95 acquired between time t6 and time t7. The processor 7 can generate the input image 96, for example, by preprocessing the ultrasonic image 95 acquired just before time t7. After the input image 96 is generated, the process proceeds to step ST12.

In step ST12, the processor 7 deduces a location indicated by the input image 96 using the trained model 33. The processor 7 inputs the input image 96 into the trained model 33 and uses the trained model 33 to deduce the sites contained in the input image 96. In the deduction step, the processor 7 calculates the probability that each imaging site is included in the input image 96. Furthermore, the processor 7 then deduces the imaging site in the input image 96 based on the probability calculated for each imaging site.

It can be assumed that the kidney probability exceeds the threshold value. Therefore, the processor 7 deduces that the imaging site included in the input image 96 is the kidney. After deducing the imaging site, the process proceeds to step ST30.

In step ST30, the processor 7 determines whether to change the imaging conditions based on the deduced imaging site. Step ST30 will be described below in detail.

First, in step ST31, the processor 7 determines whether the currently set imaging conditions are those corresponding to the imaging site deduced in step ST12. At time t7, the set imaging condition is the imaging condition for the liver (N). On the other hand, the imaging site deduced in step ST12 is the kidney. Therefore, at time t7, the set imaging conditions (imaging conditions for the kidney) are not the imaging conditions corresponding to the imaging site (liver (N)) deduced in step ST12, so the process proceeds to step ST33.

In step ST33, as depicted in FIG. 22, the processor 7 identifies the category corresponding to the deduced imaging site from among the plurality of categories 1 to N registered in the database. Here, the deduced imaging site is the "kidney", so the processor 7 identifies category 4, which includes the parameter set of the kidney, from among the a plurality of categories 1 to N.

Next, the processor 7 identifies the category corresponding to the currently set imaging conditions from among the plurality of categories 1 to N registered in the database.

Here, the currently set imaging conditions are for the liver (N), so the processor 7 identifies category 4, which contains the parameter set for the liver (N), from among the plurality of categories 1 to n. After identifying category 4, the process proceeds to step ST34.

In step ST34, the processor 7 determines whether the two categories identified in step ST33 match. If the categories match, the process proceeds to step ST32, while if the categories do not match, the process proceeds to step ST35. Here, the identified categories match (category 4), so the process proceeds to step ST35.

In step ST35, the processor 7 makes a determination to change the imaging conditions. In other words, the processor 7 makes a determination to change the imaging conditions if the categories are found not to match. The reason is described below.

Category 4 includes liver (N) parameter set D1, liver (L) parameter set D2, kidney parameter set D3, and intestine parameter set D4. The liver, kidneys, and intestines, which are the imaging targets of these parameter sets, are anatomically distinct organs. However, the values of the parameters used in liver, kidney, and intestinal imaging are often identical or close to each other. Therefore, if the currently set imaging conditions Y1 for the liver (N) are not changed to the deduced imaging conditions for the kidney, and ultrasonic images of the kidney are acquired without changing the imaging conditions for the liver (N), the image quality of the ultrasonic images is not expected to be significantly affected. Therefore, in step ST32, a determination is made not to change the imaging conditions, and the process 44 is terminated.

Therefore, the user 51 continues the examination of the kidney of the subject S43 under the imaging conditions for liver (N) from time t7 and later. On the other hand, the processor 7 continues to periodically execute process 44 after time t7. Furthermore, when the necessary images have been acquired, the examination of the kidneys of subject S43 is terminated (at time t8).

In the fourth embodiment, Category 4 of the database includes the liver (N) parameter set D1, liver (L) parameter set D2, kidney parameter set D3, and intestine parameter set D4. The liver (N) and liver (L) are both livers as organs. In addition, the liver, kidney, and intestine are different organs from each other, but the imaging conditions are not that different. Thus, ultrasonic images of the liver (N), liver (L), kidney, and intestine can be obtained with constant quality regardless of which parameter set is used, namely liver (N) parameter set D1, liver (L) parameter set D2, kidney parameter set D3, or intestine parameter set D4. Therefore, in the fourth embodiment, the liver (N) parameter set D1, liver (L) parameter set D2, kidney parameter set D3, and intestine parameter set D4 are classified to the same category 4. By classifying parameter sets D1 to D4 into the same category 4, the frequency of automatic changes in imaging conditions at timing unintended by the user 51 can be reduced because imaging conditions are not changed between the liver (N), liver (L), kidney, and intestine. In addition, since the parameter values of the liver (N) parameter set D1, liver (L) parameter set D2, kidney parameter set D3, and intestine parameter set D4 are identical or similar, ultrasonic images of sufficient quality can be obtained without any changes in imaging conditions between the liver (N), liver (L), kidney, and intestine.

What is claimed is:

1. An ultrasonic diagnostic device, comprising:
   an ultrasonic probe; and a processor configured to communicate with the ultra-sonic probe;

wherein the processor is configured to:

set imaging conditions for acquiring an ultrasonic image of a subject;

control the ultrasonic probe to transmit an ultrasonic beam towards the subject and to receive an echo signal from the subject in accordance with the imaging conditions;

generate the ultrasonic image of the subject based on the echo signal received by the ultrasonic probe;

identify one or more imaging sites included in the ultrasonic image; and determine whether to change the imaging conditions based on the identified one or more imaging sites, wherein the processor is configured to maintain the imaging conditions based on a determination that the ultrasonic image contains a plurality of imaging sites.

2. The ultrasonic diagnostic device according to claim 1, wherein the processor is further configured to:

generate an input image to be input to a trained model based on the ultrasonic image;

input the input image to the trained model to identify the one or more imaging sites included in the input image; and determine whether a number of the one or more imaging sites identified in the input image is one or is two or more; and based on a determination that the number of the one or more imaging sites identified in the input image is two or more, maintain the imaging conditions.

3. The ultrasonic diagnostic device according to claim 2, wherein the processor is further configured to:

change the imaging conditions based on a determination that the number of the one or more imaging sites identified in the input image is one.

* * * * *